United States Patent
Naleway et al.

(10) Patent No.: US 10,401,361 B2
(45) Date of Patent: Sep. 3, 2019

(54) INTRACELLULAR ORGANELLE PEPTIDE TARGETED ENZYME SUBSTRATES

(71) Applicant: Marker Gene Technologies, Inc., Eugene, OR (US)

(72) Inventors: John Joseph Naleway, Eugene, OR (US); Fiona Karen Harlan, Eugene, OR (US); Jason Scott Lusk, Eugene, OR (US)

(73) Assignee: Marker Gene Technologies, Inc., Eugene, OR (US)

( * ) Notice: Subject to any disclaimer, the term of this patent is extended or adjusted under 35 U.S.C. 154(b) by 0 days.

(21) Appl. No.: 15/837,410

(22) Filed: Dec. 11, 2017

(65) Prior Publication Data
US 2018/0120317 A1    May 3, 2018

Related U.S. Application Data

(60) Division of application No. 14/689,576, filed on Apr. 17, 2015, now Pat. No. 9,841,426, which is a continuation-in-part of application No. 13/986,535, filed on May 14, 2013, now Pat. No. 9,677,115, which is a division of application No. 12/381,560, filed on Mar. 11, 2009, now Pat. No. 8,460,862.

(60) Provisional application No. 62/176,131, filed on Feb. 9, 2015, provisional application No. 61/995,671, filed on Apr. 17, 2014.

(51) Int. Cl.
| | |
|---|---|
| *G01N 33/573* | (2006.01) |
| *A61K 47/64* | (2017.01) |
| *A61K 31/445* | (2006.01) |
| *C07K 7/06* | (2006.01) |
| *C07K 7/08* | (2006.01) |
| *C12Q 1/34* | (2006.01) |
| *G01N 33/50* | (2006.01) |
| *G01N 33/531* | (2006.01) |
| *G01N 33/58* | (2006.01) |

(52) U.S. Cl.
CPC ......... *G01N 33/573* (2013.01); *A61K 31/445* (2013.01); *A61K 47/64* (2017.08); *A61K 47/645* (2017.08); *C07K 7/06* (2013.01); *C07K 7/08* (2013.01); *C12Q 1/34* (2013.01); *G01N 33/5076* (2013.01); *G01N 33/531* (2013.01); *G01N 33/582* (2013.01)

(58) Field of Classification Search
None
See application file for complete search history.

(56) References Cited

U.S. PATENT DOCUMENTS

| | | | | |
|---|---|---|---|---|
| 8,460,862 B2* | 6/2013 | Coleman | .................. | C12Q 1/34 435/18 |
| 2004/0146959 A1* | 7/2004 | Graham | ............... | C07K 5/1013 435/15 |
| 2008/0267977 A1* | 10/2008 | Fey | ......................... | A61K 31/19 424/174.1 |
| 2010/0233744 A1* | 9/2010 | Coleman | .................. | C12Q 1/34 435/18 |
| 2011/0117588 A1* | 5/2011 | Tanaka | ..................... | C12Q 1/34 435/23 |
| 2013/0029325 A1* | 1/2013 | Kurosawa | ......... | G01N 33/56966 435/6.1 |

* cited by examiner

*Primary Examiner* — Susan M Hanley
(74) *Attorney, Agent, or Firm* — Timothy L. McCutcheon

(57) ABSTRACT

This invention relates to substrates and methods for the visualization of intracellular organelles, such as the lysosome, peroxiosome, nucleus, Endoplasmic Reticulum and Golgi Apparatus, based upon organelle enzyme activity. Such compounds represent a novel combination of chemically distinct enzyme substrates with targeting and detection substrates which are activated by enzyme activity inside target organelles to produce a detectable signal. The organelle targeted enzyme substrates of this invention are designed to provide high fluorescence at lower pH values found in some organelles and can be used for monitoring enzyme activity inside cells at very low concentrations.

15 Claims, 4 Drawing Sheets
Specification includes a Sequence Listing.

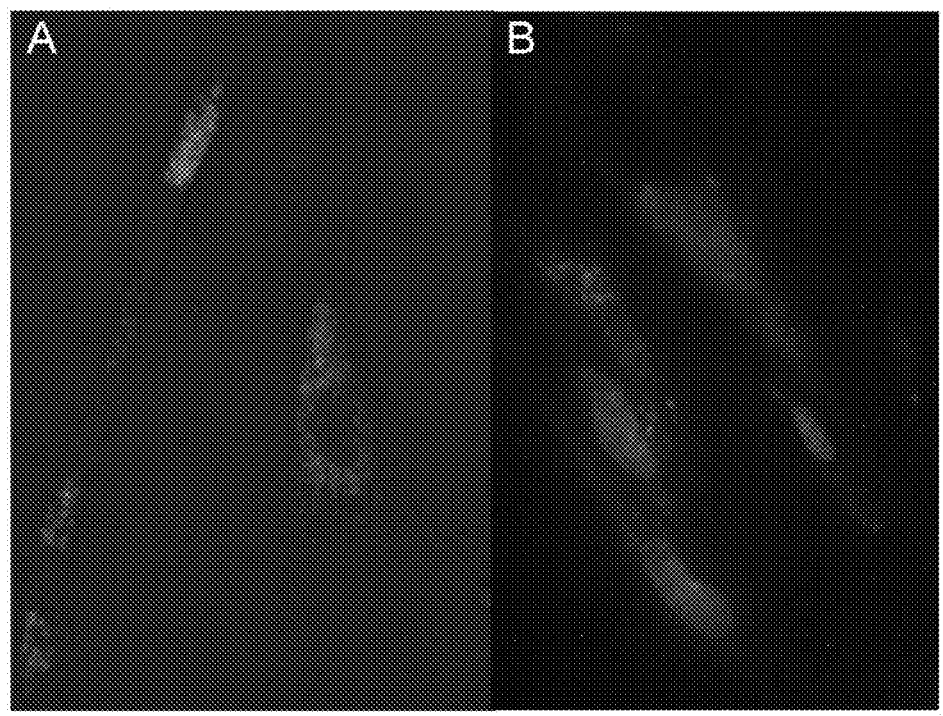
Figure 1. Representative staining of ER (A) and Golgi (B) with targeted resorufin alpha-mannosidase substrates.

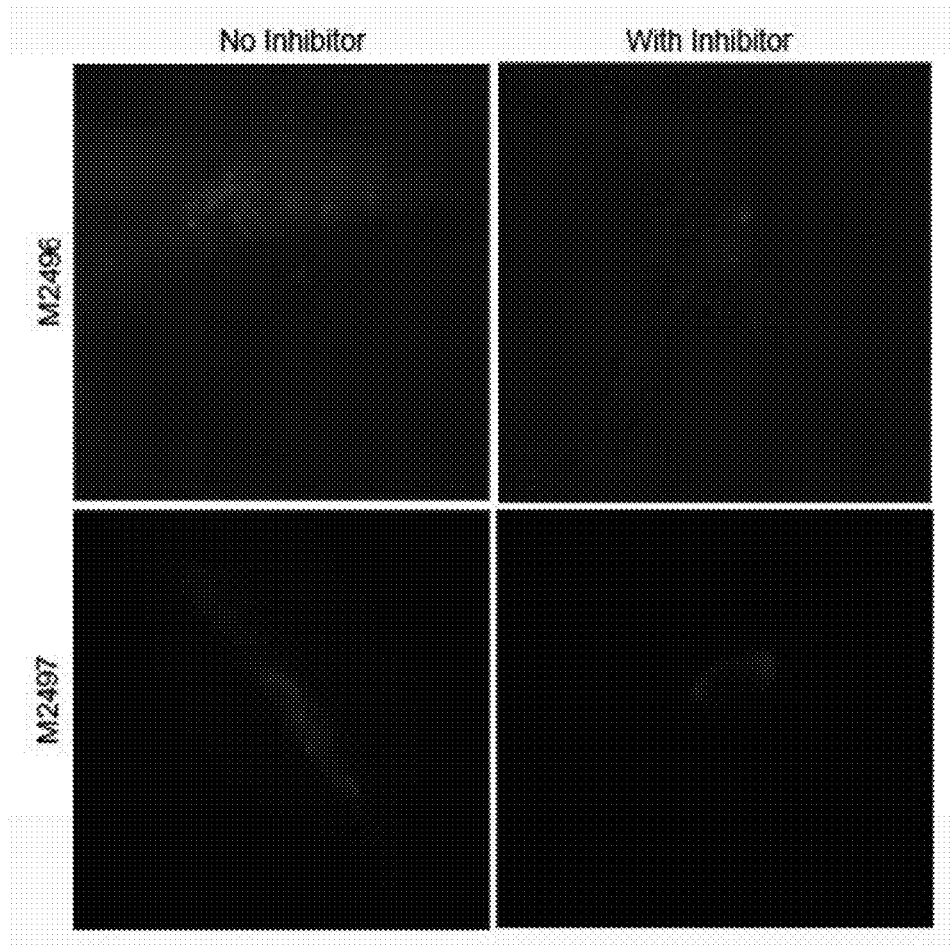
Figure 2. Staining with targeted Mannosidase substrates following enzyme inhibition.

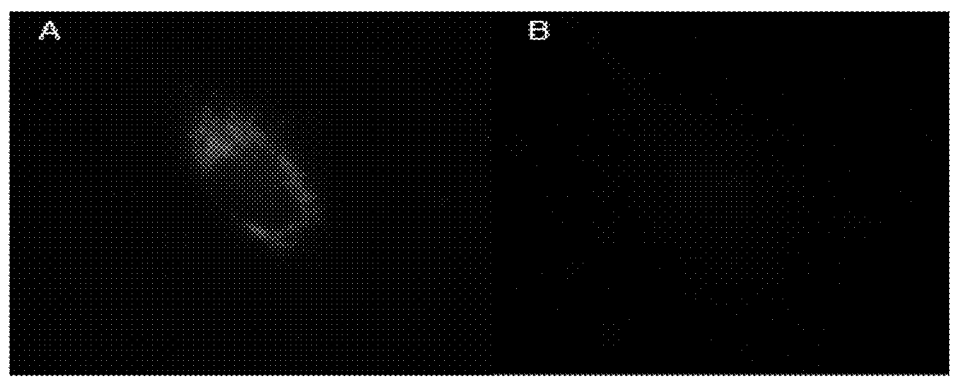
Figure 3. Staining of Gaucher II (A) and Healthy (B) fibroblasts with ER targeted glucosidase substrate.

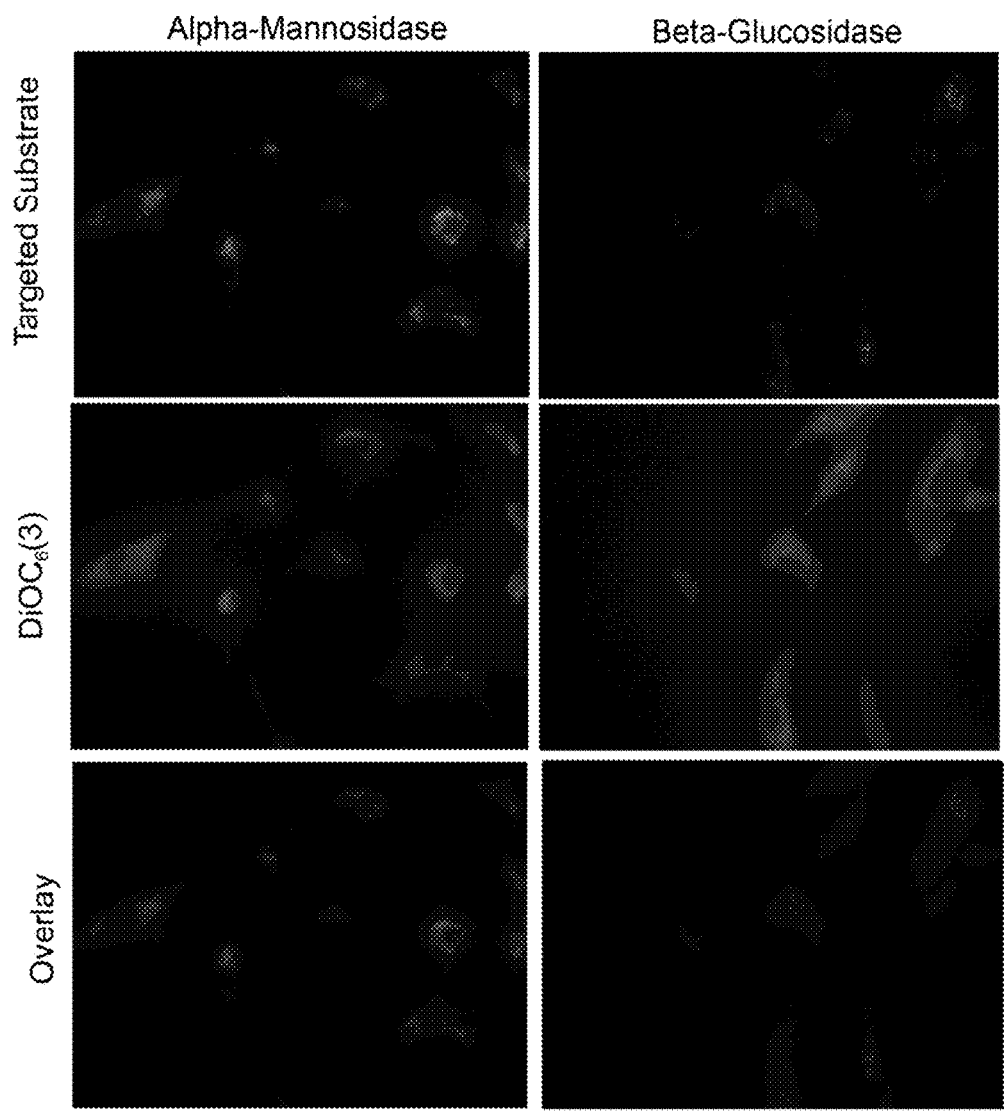
Figure 4. Colocalization of ER targeted substrates and a known ER stain.

INTRACELLULAR ORGANELLE PEPTIDE TARGETED ENZYME SUBSTRATES

CROSS-REFERENCE TO RELATED APPLICATIONS

The present application is a divisional of application U.S. Ser. No. 14/689,576 filed Apr. 17, 2015 which issued as U.S. Pat. No. 9,841,426 on Dec. 12, 2017, which is a continuation-in-part of application U.S. Ser. No. 13/986,535 filed May 14, 2013 which issued Jun. 13, 2017 as U.S. Pat. No. 9,677,115, which is a divisional of application U.S. Ser. No. 12/381,560, filed Mar. 11, 2009 which issued as U.S. Pat. No. 8,460,862. The present application also claims priority in Provisional application U.S. Ser. No. 62/176,131 filed Feb. 9, 2015.

This invention was made with Government support under grant 1R43GM108137-01 and grant 5R43MH079542-02 awarded by the National Institutes of Health. The Government has certain rights in this invention.

REFERENCE TO SEQUENCE LISTING

The present invention includes a sequence listing submitted in Computer Readable Form (CRF) which is hereby incorporated by reference. The CRF includes a single file of 5 KB denoted "MGT-2-C1 sequences_ST25.txt" recorded on Apr. 10, 2015.

FIELD OF THE INVENTION

This invention relates substrates and methods for the fluorescent staining of intracellular organelles based upon organelle enzyme activity. The fluorescent organelle substrates of the invention are specific for enzyme activity of the organelle and label these organelles, including but not limited to lysosomes, peroxiosomes, nucleus, endoplasmic reticulum and Golgi apparatus, rendering them fluorescent and easily observed.

BACKGROUND OF THE INVENTION

Acidic organelles are present in all cells and tissues of mammalian, plant, yeast and fungal cells, except red blood cells. Many bacteria also contain acidic compartments. These acidic organelles are often involved in metabolism and catabolism of foreign molecules that are brought into the cell by endocytosis. They are often the first line of defense against foreign bacterial or viral infection. The acidic pH of endosomes is critical to the process by which lipid-enveloped viruses enter the cytoplasm after their cellular uptake by receptor-mediated endocytosis. Phagocytosis is the process where extra cellular particles such as bacteria, are engulfed in the cell and then fused to lysosomes for digestion. Acidic organelles have also been shown to be responsible for digestion of high molecular weight proteins, oligosaccharides, glycolipids or peptides by the cell. In addition, they are often involved in therapeutic drug metabolism. Among the cellular organelles that have been found to mediate their enzyme activities by acidification are lysosomes, acidic endosomes, phagosomes, clathrin-coated vesicles and Golgi vescicles.

The Golgi Apparatus and the Endoplasmic Reticulum (ER) are dynamic organelles involved in the synthesis, processing and sorting of cellular proteins and lipids. The Golgi and ER are also involved in a great number of cellular processes including proprotein activation, glycoconjugate modification, glycolipid synthesis, phosphorylation and sulfation of proteins and sugars as well as sorting and trafficking of newly synthesized proteins internally or as part of the secretory pathway. Both organelles have been implicated in defense against pathogens, cholesterol homeostasis, metabolism, apoptosis and cell signaling. As such, the Golgi and the ER contain a great number of metabolic and regulatory enzymes that are involved in ordered function and processing of nearly all proteins, lipids, and carbohydrates in the cell. And more information is continually accumulating that functional deficiencies or mutations in these enzymes are indicative of a number of disease states, particularly those that affect the nervous system such as Alzheimer's Disease, Parkinson's Disease, ALS, Lowe Syndrome, I Cell Disease, Globoid Cell Leukodystrophy, Adrenoleukodystrophy, Niemann-Pick Disease, Metachromatic Leukodystrophy, Mannosidosis and Cystic Fibrosis as well as proliferative diseases, viral infections and neoplastic growth and metastasis.

Prior stains, methods and assays for visualizing acidic organelles are not useful for monitoring enzyme activities in living cells. For example, weakly basic amines have been shown to selectively accumulate in cellular compartments with low internal pH. When further linked to chromogenic or fluorogenic probes, they can be used to label these compartments. Among these is the frequently used acidotropic probe, N-(3-((2,4-dinitrophenyl)amino)propyl)-N-(3-aminopropyl)methylamine, dihydrochloride (hereafter referred to as DAMP). The fluorescent dyes neutral red and acridine orange are also commonly used for staining acidic organelles, but they lack specificity and are not well retained in the organelles, particularly after fixing and permeabilization.

In particular, methods to analyze Golgi and ER enzyme functional activity within living cells have been hampered by the inability to monitor such activity inside individual organelles. The instant invention intends to address this problem by the use of new, organelle-targeted, live-cell assay systems for Golgi and ER enzyme activities that can be used for discovery and testing of new therapeutic agents for neurodegenerative, proliferative, cardiac diseases or infections. Many ER and Golgi enzymes are under investigation as drug targets for affecting intracellular processing and synthesis mechanisms and thereby provide novel therapeutics for the mentioned and other related diseases.

Tools for staining the Golgi or ER using fluorescence microscopy include recombinant fluorescent proteins that have luminal targeting peptide sequences for the Golgi and ER as well as dye derivatives (e.g. Brefeldin A (BFA) conjugates) that are selectively localized on the cytosolic face of the Golgi and ER in many different cell lines. The peptide sequences identified to target recombinant proteins have also been used to target fluorophores to the Golgi and ER in live cell assays. These dyes are retained in the Golgi and ER due to the presence of specific C-terminal signal sequences such as KDEL (SEQ ID NO:1) or SDYQRL (SEQ ID NO:2) or related sequences that are inserted into the luminal face of the ER or trans-Golgi network. Fluorescently labeled peptides containing these sequences can visualize intracellular processes and molecular interactions at a single-cell level. Protein systems containing these targeting sequences have been used to measure the intra-organelle pH of the ER and Golgi (Wu, et al., 2000). Many other peptide sequences have also been identified for targeting to other organelle structures within living cells. The present invention proposes to utilize these established systems to target fluorogenic enzyme substrates to specific organelles for live-cell analysis of enzyme activity.

The present invention utilizes fluorogenic enzyme substrates for the labeling and tracing metabolic and defective activities in these organelles in live cells or in cell-free systems. These new substrates selectively accumulate in cellular compartments based upon selective targeting sequences and can be used to investigate the enzyme levels responsible for biosynthesis, degradation and recycling of cellular components and for measuring specific enzyme defects involved in a number of human diseases linked to enzyme activity in particular organelles within live cells.

Peptide motifs that can be used to target proteins or even small molecules to various locations within cells are known in the art. For example, the nuclear targeting sequence from the SV40 large T antigen PKKKRKV SEQ ID NO:3 has been used to localize exogenously delivered macromolecular conjugates to live cells as well as recombinant proteins expressed after plasmid or viral DNA transfection/transduction.

Peptide localization motifs have also been described for organelles other than the nucleus. For example, the four amino acid sequence KDEL (SEQ ID NO:1) at the amino terminus of a protein is a well established ER-retention sequence while the carboxy-terminal sequence of amino acids containing SKL has been identified for peroxisomal targeting. These and other targeting sequences have been used for fluorescent labeling of specific organelles in live cells as an orthogonal method to cell staining by conjugation to small molecule organic dyes. These peptide sequences are known to be actively transported into living cells by the method of retrograde transport Recently these same peptide motifs have been cloned into fluorescent proteins for specific staining of individual organelles when expressed inside living cells. While such targeting peptides or proteins have been used as research tools for staining specific organelles their potential for real time analysis of enzyme activity within living cells or tissues remains unexplored.

The organelle targeted enzyme substrates of this invention are designed to provide high fluorescence at lower pH values found in some organelles and contain further derivatized groups to support membrane permeation through both outer and organelle membranes of intact cells. They can be used for monitoring enzyme activity in cells at very low concentrations and are not toxic to living cells or tissues. The instant dyes, substrates and methods for their use are described herein for investigating metabolism, monitoring enzyme activities associated with diseases, for analysis of the biogenesis or degenerative states of organelles, the development of, investigating development of cells or cultured neurons, and detecting pH gradients. The current invention is also useful for labeling non-mammalian cells that possess the targeted organelles, including bacteria, yeast, spermatozoa and plant cells, or for the labeling and analysis of enzyme activity in symbiotic or invasive bacterial species that predominantly partitions to specific organelles within living cells.

SUMMARY OF THE INVENTION

The present invention includes methods and describes the synthesis of materials for analysis of organelle enzyme activities, whether present in cells or in isolated cell-free organelle preparations, using fluorogenic enzyme substrates that produce a visible signal when acted upon by such enzymes. The method includes: preparing a labeling solution containing the targeted fluorogenic enzyme substrate or substrates, where the fluorescent labeling solution includes a substituted fluorescent dye having high fluorescence at low pH values and possessing a covalently attached peptide sequence moiety and is derivatized for specific enzyme analysis; and incubating with a sample comprising isolated cellular organelles, or by incubation with live cells or tissues, allowing the labeling solution a sufficient time to produce fluorescent labeling of the organelles and reading the fluorescence using any number of common fluorescence detection systems. Two or more of the targeted fluorogenic enzyme substrates may be incubated with the cell sample to measure two independent enzyme activities simultaneously.

The fluorogenic acidic organelle enzyme substrates of this invention are designed to provide high fluorescence at low pH values and are derivatized to permit membrane permeation through both outer and organelle membranes of intact cells. Such substrates can be used for staining cells at very low concentrations and are not toxic to living cells or tissues. The instant substrates and methods are useful for investigating metabolism, biogenesis of organelles, monitoring changes in organelle enzyme activities including enzyme activities associated with diseases, evaluating the relative levels of enzymes in both normal and diseased states and detecting pH gradients within organelles.

BRIEF DESCRIPTION OF THE DRAWINGS

FIG. 1. Representative staining of ER (A) and Golgi (B) with targeted resorufin alpha-mannosidase substrates.

FIG. 2. Staining with targeted Mannosidase substrates following enzyme inhibition.

FIG. 3. Staining of Gaucher II (A) and Healthy (B) fibroblasts with ER targeted glucosidase substrate.

FIG. 4. Colocalization of ER targeted substrates and a known ER stain.

DESCRIPTION OF THE PREFERRED EMBODIMENTS

The present invention proposes to expand the uses of standard fluorogenic, chromogenic or chemiluminescent assay systems beyond their conventional measurement applications to facilitate the detection of enzymes inside specific organelles of living cells and tissues and to investigate the relation of differential enzyme activities to their involvement in various disease states. The instant reagents and methods combine two interconnected lines of biochemistry. In particular, enzyme substrates known to be acted upon by endogenous enzymes found within organelles are combined with intracellular targeting of the detection compounds. These new substrates selectively accumulate in targeted cellular compartments and, when acted upon by enzyme activity inside the target organelle, produce a detectible signal in relation.

The targeted organelle substrates of the present invention have the general formula:

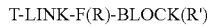

Where T represents a Targeting group that is a peptide sequence containing an amino acid sequence that partitions the substrate or dye to the specific organelle, F represents the fluorophore that has further elaboration with substituent or substituents R to provide for increased fluorescence or stability under physiological or observation conditions and BLOCK represents a biological molecule that can be removed by specific enzyme activity within the targeted organelle within a living cell or in a fixed cell or isolated organelle preparation.

BLOCK represents a biological molecule including a carbohydrate, aminoacid, peptide, phosphate, sulfate, lipid or nucleic acid group. The BLOCK group can be further modified with a substituent or substituents that improve membrane permeability of the substrate through cellular membranes.

The substituent or substituents R, which may be the same or different, are selected from the group hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl or alkynyl; or a LINK-T moiety.

Preferably, the substituent or substituents R that are not a LINK-T moiety include electron-withdrawing groups such as, halogen, cyano, alkyl, aryl, heteroaryl, alkenyl or may be a hydrogen. More preferably, the substituent or substituents R that are not a LINK-T moiety are halogen, aryl or cyano. Alternatively, for those dyes where R is linked to a fused aromatic 6-membered ring that is optionally and independently substituted one or more time, at any position, by halogen, cyano, alkyl, perfluoroalkyl, alkoxy, alkenyl, alkynyl, cycloalkyl, alkylthio, alkylamido, amino, monoalkylamino, dialkylamino, carboxamide, hydroxy, mercapto, aryl, heteroaryl, aryl-amido, heteroaryl-amido, aryl-oxy, heteroaryl-oxy, aryl-amino, or heteroaryl-amino, or 1-2 additional fused benzo or heteroaromatic rings that are themselves optionally further substituted by halogen, amino or carboxamide. Any of the fused aromatic 6-membered rings or additional fused benzo or heteroaromatic rings is optionally substituted one or more times by a LINK-T moiety.

As used herein, aryl is an aromatic or polyaromatic substituent containing 1 to 4 aromatic rings (each ring containing 6 conjugated carbon atoms and no heteroatoms) that are optionally fused to each other or bonded to each other by carbon-carbon single bonds. Each aryl is bound to the dye by a single bond, and is optionally substituted as described below.

As used herein, a heteroaryl is an aromatic group that contains at least one heteroatom (a non-carbon atom within the ring structure). Each heteroaryl is a single 5- or 6-member ring, or is a fused 2- or 3-ring structure. The heteroaryl group contains one or more heteroatoms, e.g. as pyrrole, thiophene, or furan (single ring, single heteroatom), or oxazole, isoxazole, oxadiazole, or imidazole (single ring, multiple heteroatoms), or benzoxazole, benzothiazole, or benzimidazole (multi-ring, multiple heteroatoms), or benzofuran or indole (multi-ring, single heteroatom). Each heteroaryl is bound to the dye by a single bond, and is optionally substituted as described below.

Any aryl, heteroaryl, aryl-amido, heteroaryl-amido, aryl-oxy, heteroaryl-oxy, aryl-amino or heteroaryl-amino substituent on the dye itself, or present on a substituent, is optionally and independently substituted one or more times by halogen, amino, carboxamide, hydroxy or mercapto.

Any of said alkenyl or alkynyl substituents independently has 2-6 carbons, and is optionally substituted by halogen, alkyl, cyano, carboxylate ester, carboxamide, aryl, heteroaryl, or additional alkenyl or alkynyl groups. Preferably an alkenyl group is an ethenyl, dienyl or trienyl group.

Each of the alkyl substituents, as well as the alkyl portions of alkoxy, cycloalkyl, arylalkyl, alkylamino, alkylthio or alkylamido substituents independently has 1-6 carbons, and is optionally substituted by halogen, amino, alkylamino, dialkylamino, carboxamide, hydroxy, mercapto or cyano.

For all embodiments, at least one of the R substituents is a LINK-T moiety, a LINK-T substituted methine, or one of the dye substituents that is a fused 6-membered ring is further substituted by a LINK-T moiety. For all embodiments, where the dye is substituted by more than one LINK-T, they are the same or different.

The LINK portion of LINK-T is a covalent linkage, serving to attach a peptide targeting sequence, T, to the fluorophore, F. Any suitable covalent linkage that does not interfere with the ability of the dye to selectively accumulate in the targeted organelles is an acceptable covalent linkage for the purposes of the present invention. In one embodiment, LINK is a single covalent bond. Preferred LINK groups have 1-20 nonhydrogen atoms selected from the group consisting of C, N, O and S. Such LINK groups are composed of any combination of chemical bonds, including thio-conjugated maleimido, thio conjugated iodoacetyl, ether, thioether, amine, ester, carboxamide, sulfonamide, hydrazide bonds, and single, double, triple carbon-carbon bonds, and aromatic or heteroaromatic bonds. Preferred LINK groups are composed of any combination of single carbon-carbon bonds, carbon-sulfur bonds and/or carboxamide bonds. Selected specific examples of LINK optionally include methylenes, oligomethylenes, polyethyleneglycols, phenylenes, thienyls, carboxamides, and sulfonamides. In one embodiment of the invention, LINK contains 1-6 carbon atoms. In an additional embodiment of the invention, LINK has the formula —$(CH_2)_a(CONH(CH_2)_b)_z$—, where a has any value from 0-5, b has any value from 1-5 and z is 0 or 1.

Preferred LINK groups are composed of any combination of single carbon-carbon bonds and carbon-sulfur bonds. Selected specific examples of LINK optionally include methylenes, oligomethylenes, phenylenes, thienyls, polyethyleneglycols, carboxamides, and sulfonamides. In one embodiment of the invention, LINK contains 1-6 carbon atoms. In an additional embodiment of the invention, LINK has the formula —(CH2)a(N(COCH2)z-, where a has any value from 0-5 and z is 1 or 2. In an additional embodiment of the invention, LINK has the formula —(CH2)a(N(COPh CH2)-, where a has any value from 0-5.

In a particular embodiment of the invention, the T and F groups are further modified with a substituent or substituents (R and R') that improve membrane permeability of the substrate through cellular membranes. The substituent or substituents R and R', which may be the same or different, are selected from the group including an unsubstituted carboxylic acid ester and an alkyloxy substituted carboxylic acid ester. The substituents (R or R') of the present invention are lipophilic groups that are covalently attached to T or DRUG facilitate membrane permeability and live cell entry. Once inside the cells, these lipophilic groups are hydrolyzed by endogenous cell processes resulting in release of the underivatized T-LINK-F molecules that are then well retained in living cells.

In a particular embodiment, lipophilic substitutents R and R' are acetoxymethyl (AM) ester or acetate esters. Once inside the cells these groups are cleaved by nonspecific esterases resulting in active molecules.

The targeting group T is chosen from the group containing the general formulae as shown in Table 1.

TABLE 1

Peptide Targeting Groups

| Peptide (localization) | Amino acid sequence | Net charge | SEQ ID NO |
|---|---|---|---|
| PTS1 (peroxisomal) | Ac-CKGG<u>AKL</u> | +1 | 4 |
| NLS (nuclear) | Ac-VVV<u>KKKRK</u>VVC | +4 | 5 |
| KDEL (ER) | Ac-CFF<u>KDEL</u> | -2 | 6 |
| TGN (trans-Golgi network) | GA<u>SDYQRL</u>C | 0 | 7 |

As is known in the art, the organelle targeting group peptide can also be modified to improve or reduce binding to the receptor in the membrane by modifications of the peptide sequence or by using D-amino acids in the existing sequences. Some of these modifications, listed below in Table 2, can be used to improve targeting specificity.

TABLE 2

Additional peptide sequences for target group applications

| Peptide (localization) | Amino acid sequence | SEQ ID NO: |
|---|---|---|
| ER | CAHHAEL | 8 |
| ER | CARHAEL | 9 |
| ER | CPLHNEL | 10 |
| ER | CERHTEL | 11 |
| ER | CTEHIEL | 12 |
| ER | CTEHVEL | 13 |
| trans-Golgi | SDpYQRLC | 14 |
| trans-Golgi | ADYQRLC | 15 |
| trans-Golgi | SGYQRLC | 16 |
| trans-Golgi | AAYQRLC | 17 |
| trans-Golgi | SDYERLC | 18 |
| trans-Golgi | SDYQRVC | 19 |
| nuclear | AcVVVKKRRRVVC | 20 |
| nuclear | AcVVVKKRKKVVC | 21 |
| peroxisomal | AcCKGGYQSKL | 22 |
| peroxisomal | AcCKGGYQSEL | 23 |

In a preferred embodiment, T represents a targeting group comprising a peptide selected from the group consisting of -AKL-, -KKKRK- (SEQ ID NO:25), -KDEL- (SEQ ID NO:1) and -SCYQRL-(SEQ ID NO:26).

For all embodiments of the invention, the targeting group moiety T is optionally present in the form of a salt form of the carboxylic acid or amino group composition, for example the hydrochloride salt, sulfate salt, perchlorate salt, or other organic acid salts of lysine residues or the sodium or potassium salt of aspartate residues. As is known in the art, peptidomimetics of these listed peptide targeting groups may also be designed and employed for improved stability from non-specific peptidase cleavage in live cell applications.

In a preferred embodiment, the substrate for detecting enzyme activity in a sample containing cellular organelles has a formula of:

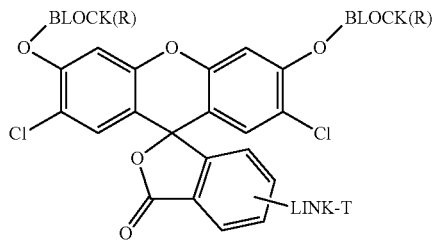

where
A) T is a peptide having an amino acid sequence selected from the group consisting of: SEQ ID NO: 1, SEQ ID NO:2, SEQ ID NO:4, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:25, and SEQ ID NO:26;
B) BLOCK is a monovalent moiety adapted to be cleaved from the remainder of the substrate by action of a specific enzyme native to said organelle, resulting in a visible signal at the site of the enzyme reaction;
C) LINK is a covalent linkage; and
D) (R) is a substituent selected from the group consisting of hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl, an unsubstituted carboxylic acid ester and an alkoxy substituted carboxylic acid ester.

In another preferred embodiment, the substrate for detecting enzyme activity in a sample containing cellular organelles has a formula selected from the group consisting of:

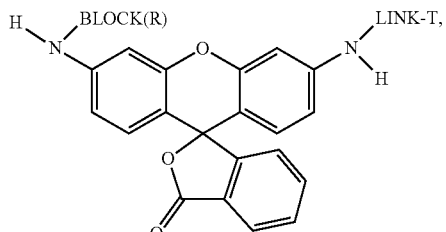

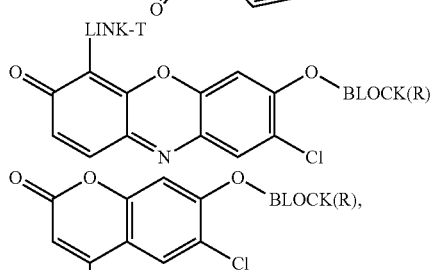

where
A) T is a peptide having an amino acid sequence selected from the group consisting of: SEQ ID NO: 1, SEQ ID NO:2, SEQ ID NO:4, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:25, and SEQ ID NO:26;
B) BLOCK is a monovalent moiety adapted to be cleaved from the remainder of the substrate by action of a specific enzyme native to said organelle, resulting in a visible signal at the site of the enzyme reaction;
C) LINK is a covalent linkage; and
D) (R) is a substituent selected from the group consisting of hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl, an unsubstituted carboxylic acid ester and an alkoxy substituted carboxylic acid ester.

Selected specific embodiments of dyes useful for the staining of organelles in living cells and in organelle extracts, or fixed cell preparations are described in Tables 3 through 10. Further elaboration or mixed complementary substitutions will be obvious to a person skilled in the art.

TABLE 3

Fluorescein Based Esterase Substrate (Green Fluorescence) Targeted to the Endoplasmic Reticulum

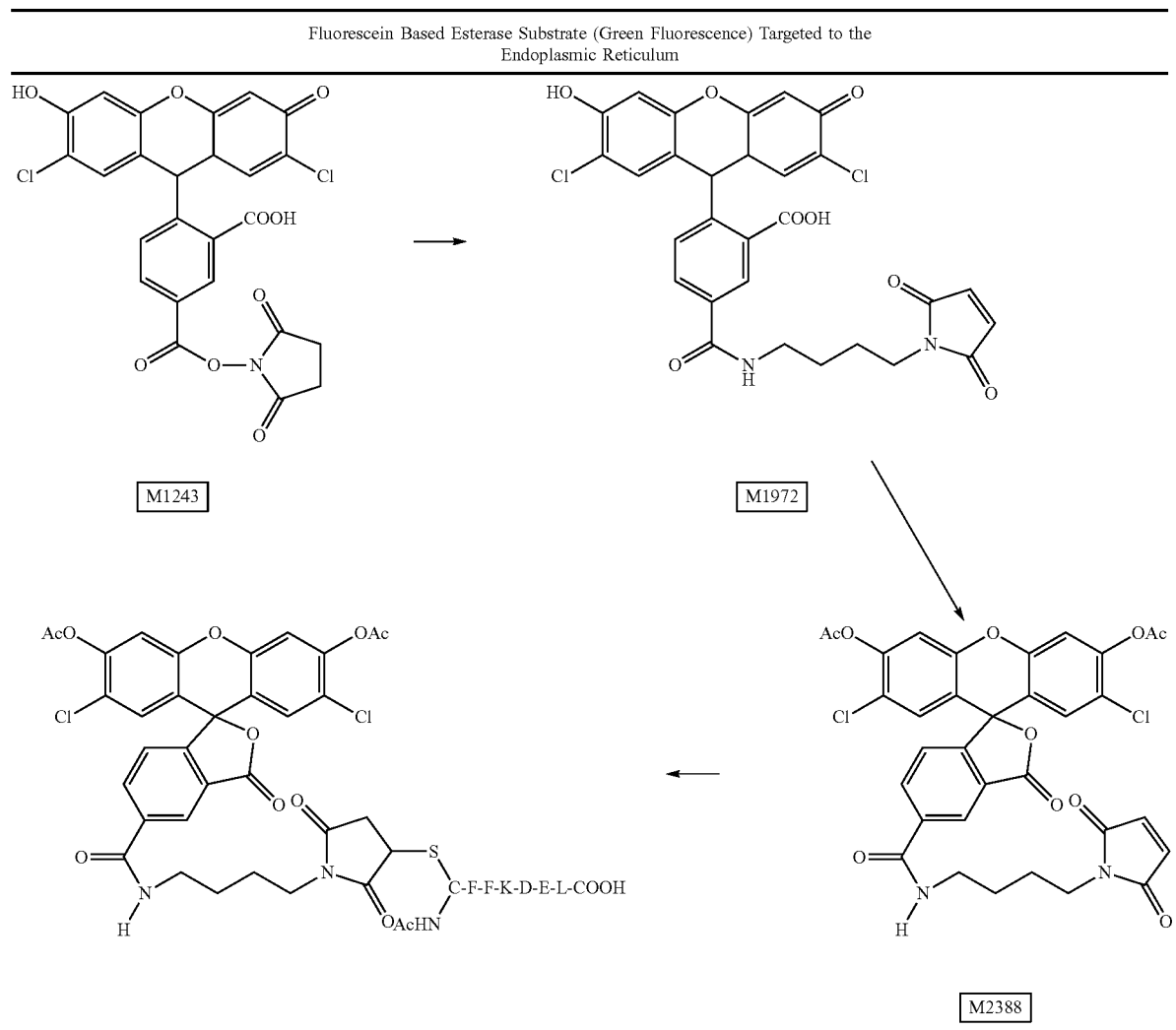

TABLE 4
Rhodamine 110 Based Furin Substrate (Green Fluorescence) Targeted to the Golgi Apparatus
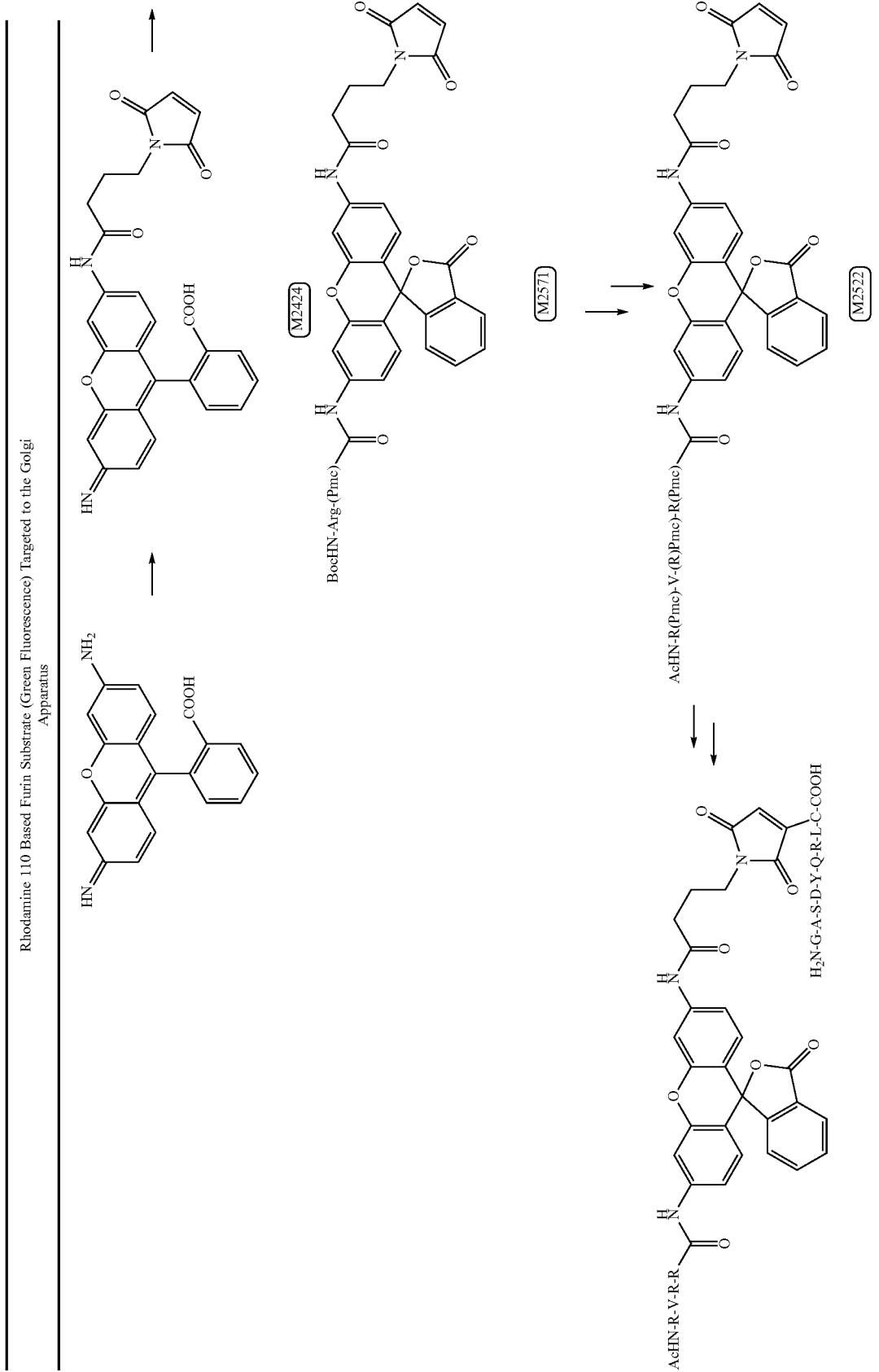

TABLE 5
Resorufin Based α-Mannosidase Substrate (Red Fluorescence) Targeted to the Endoplasmic Reticulum
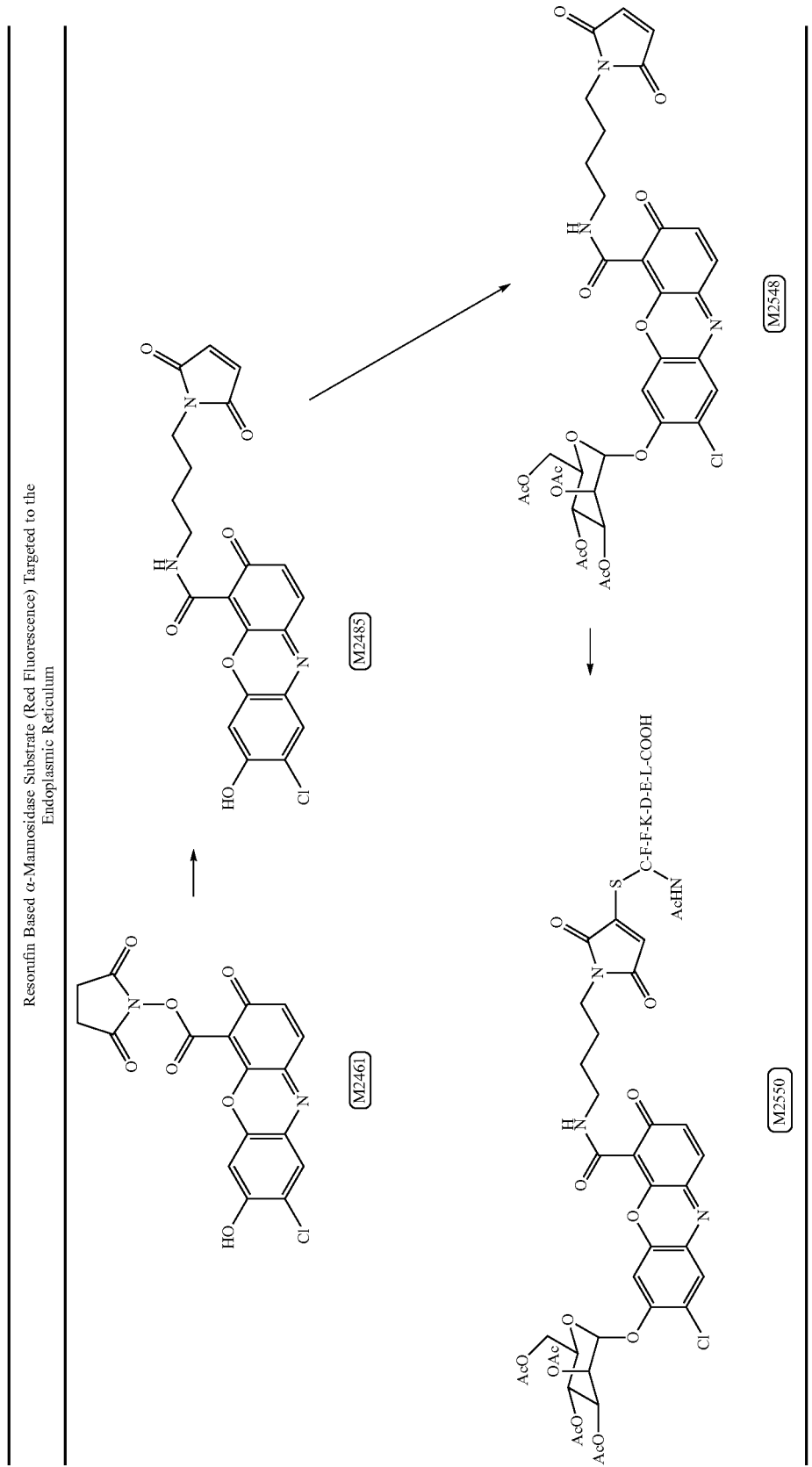

TABLE 6
Coumarin Based β-Glucosidase Substrate (Blue Fluorescence) Targeted to the Endoplasmic Reticulum
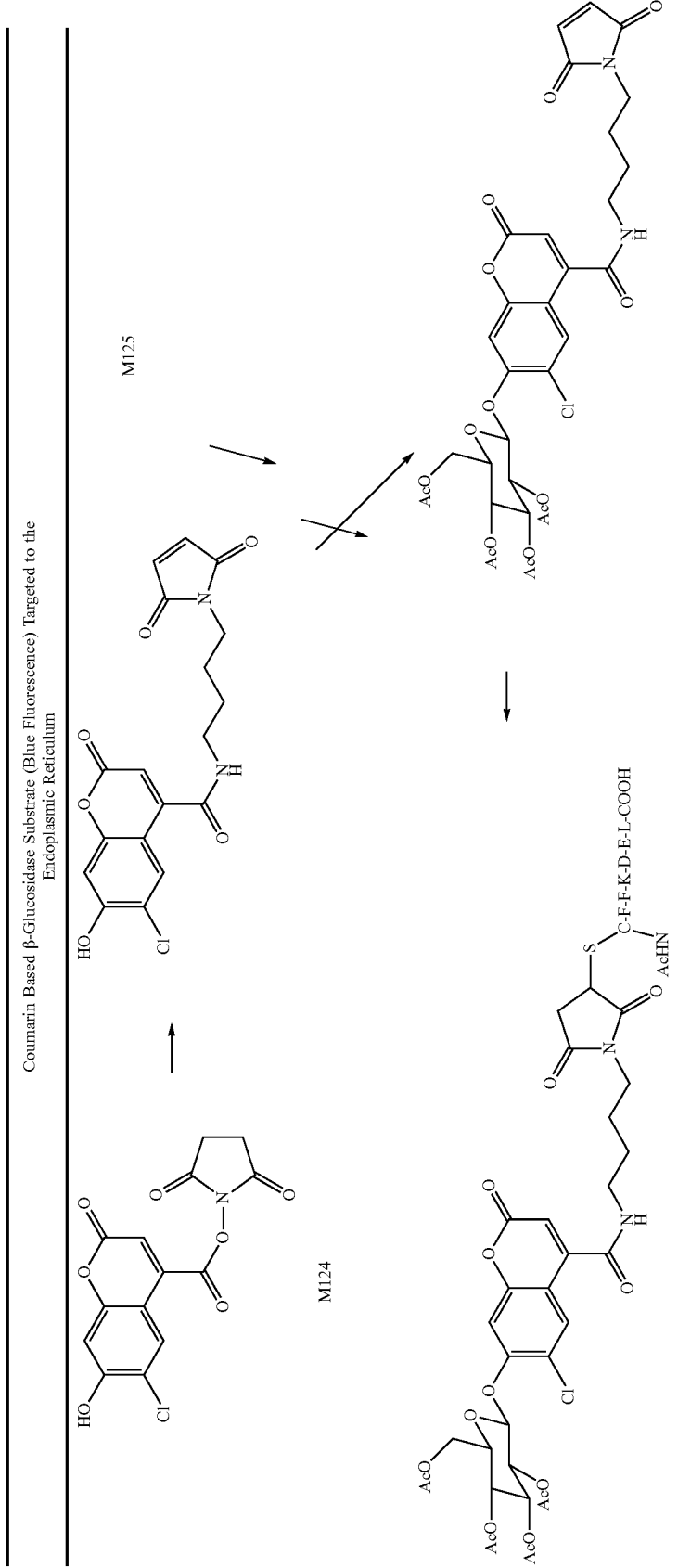

TABLE 7
7-Nitrobenzofurazan Based General Organelle Stain Targeted to the Golgi
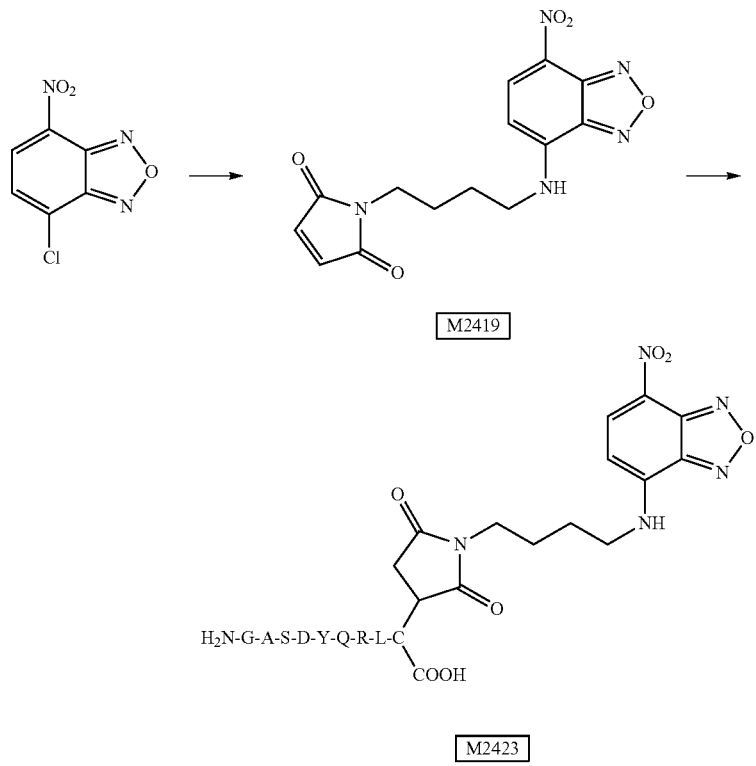

TABLE 8
Fluorescein-based (Green Fluorescence) Substrate Targeted to the ER for measurement of Phosphatase Activity
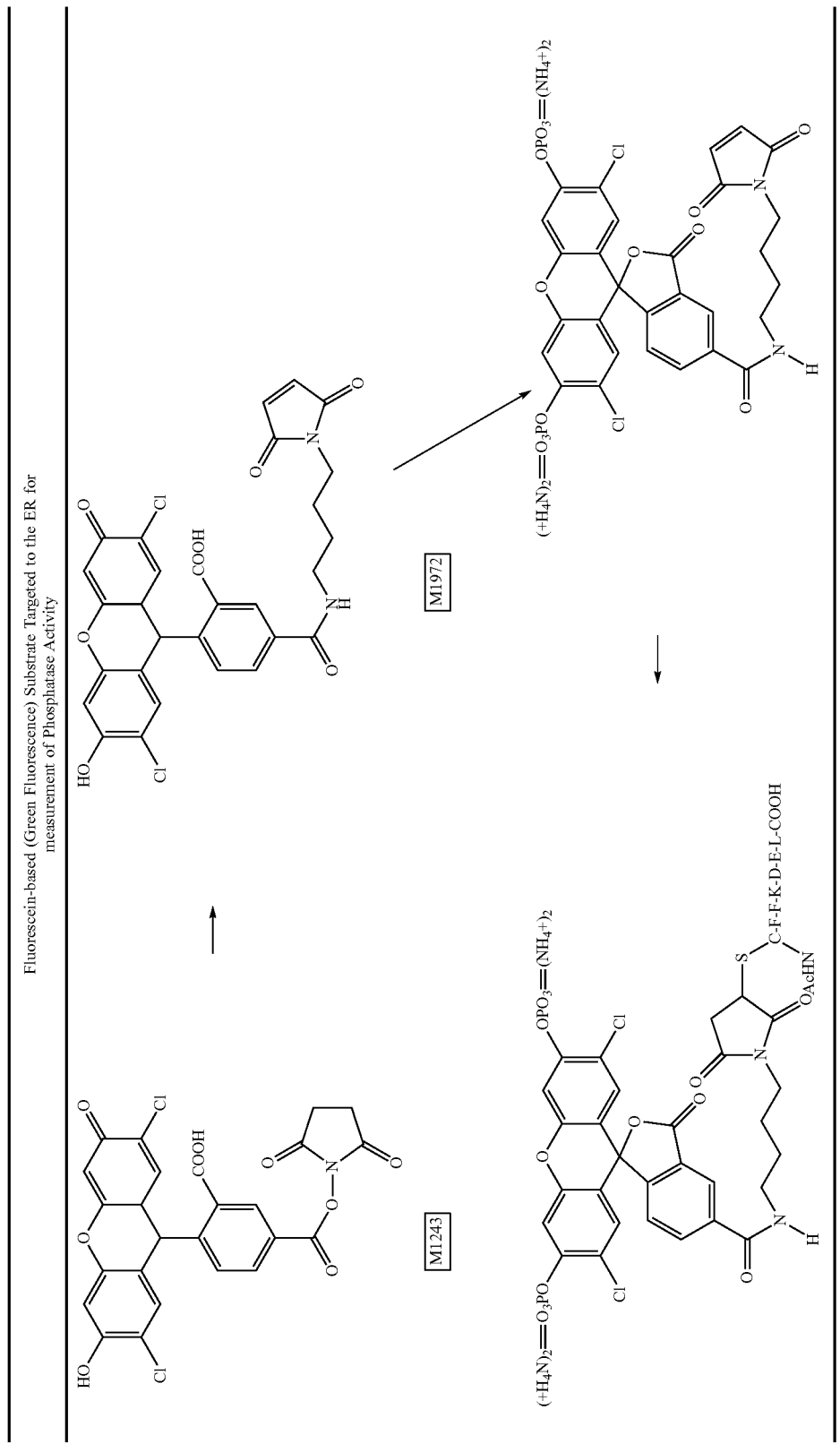

TABLE 9
Resorufin-based (Red Fluorescence) Substrate Targeted to the Golgi for Measurement of Sulfatase Activity
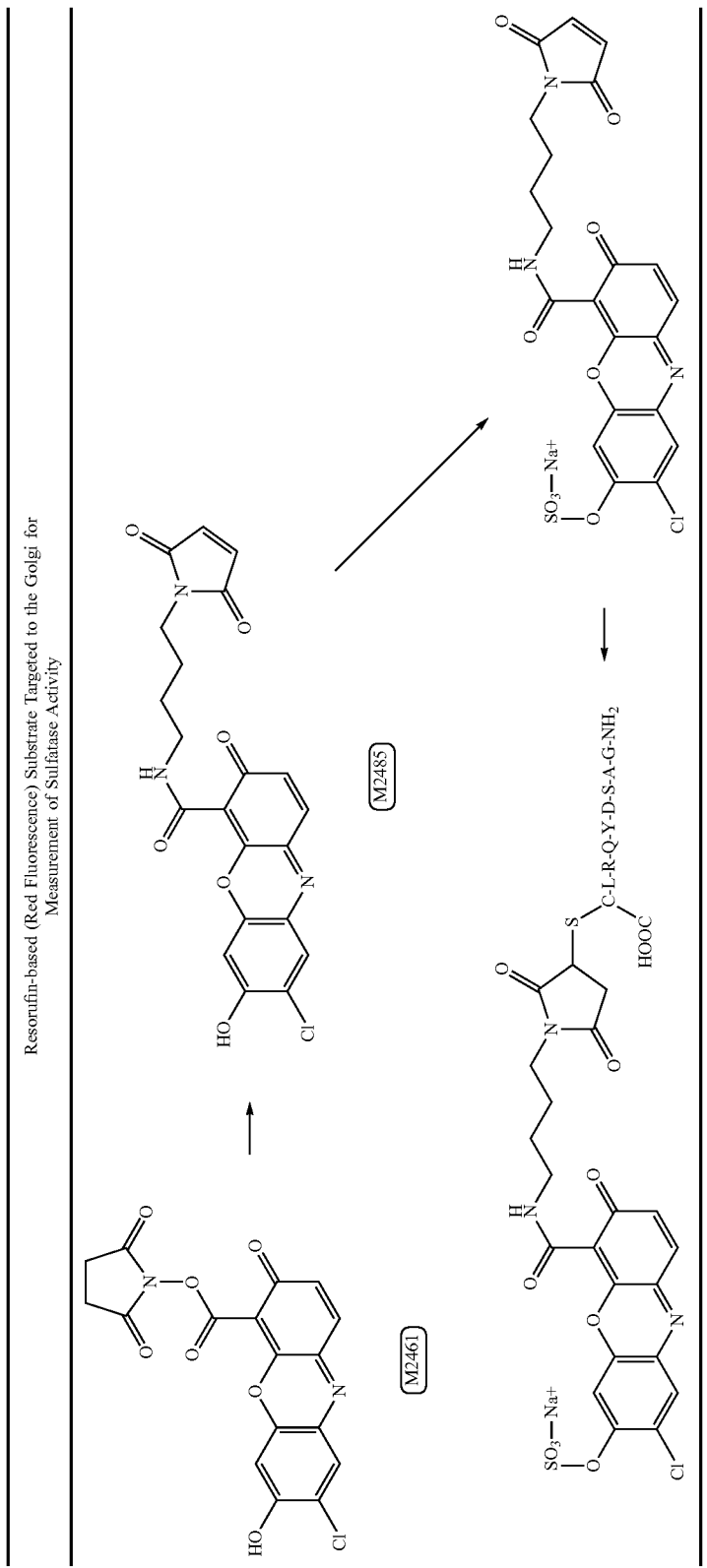

TABLE 10
Resorufin-based (Red Fluorescence) Substrate Targeted to the Golgi Apparatus for Measurement of Lipase Activity
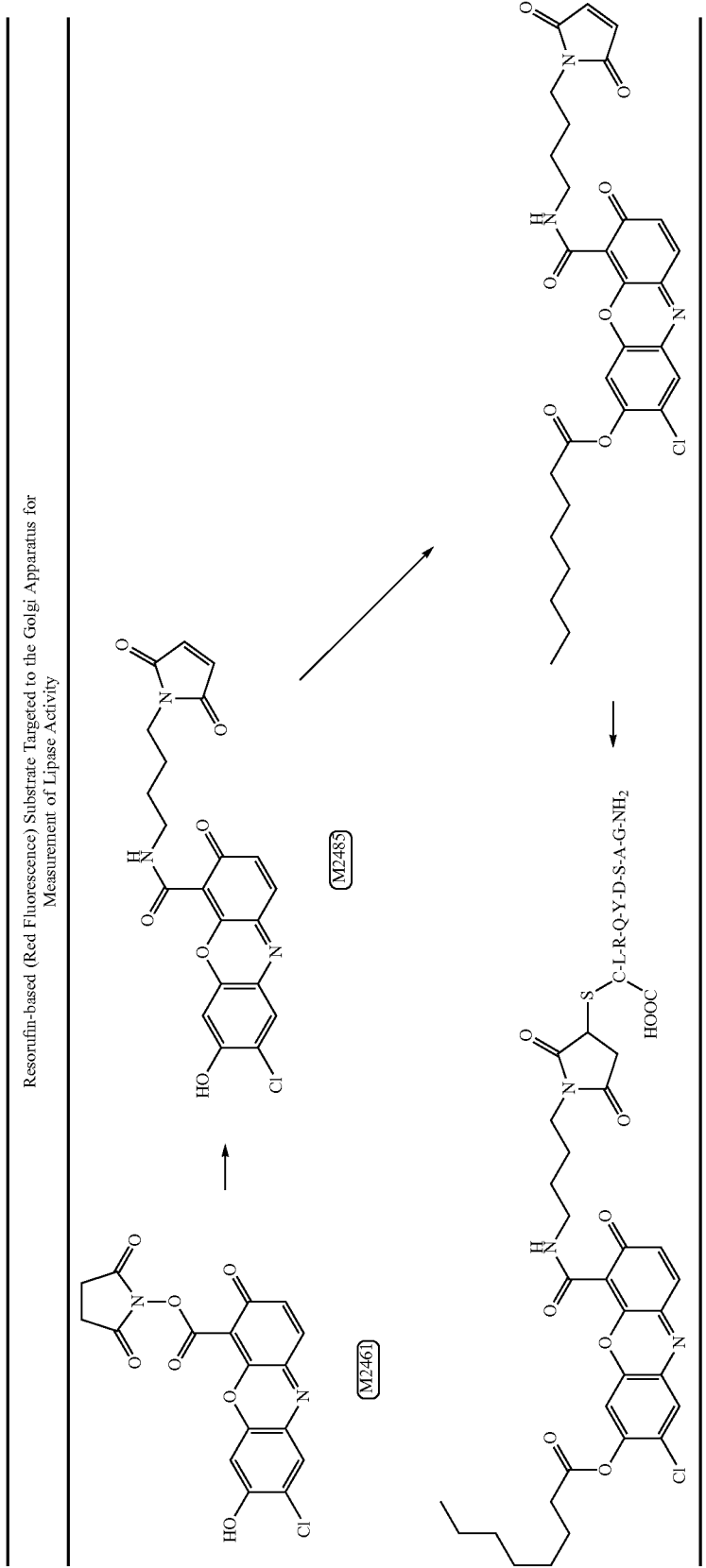

The substrates and probes of the present invention are readily prepared using the standard organic synthesis methods described herein. Specific methods for preparing the covalent linkage, LINK, and Targeting Group T are demonstrated in the Examples that follow directly.

Compounds wherein the LINK or T moiety incorporates an alternate structure are prepared by using methods that are well known in the art.

In addition to the aforementioned endoplasmic reticulum and Golgi apparatus targeting groups, the invention may also be modified via alternate peptide sequences and functionalities to target other organelles within the cell, including but not limited to: peroxisomes; nucleus; mitochondria; and lysosomes. A person skilled in the art will recognize the appropriate peptide sequences or targeting groups that might be utilized for these additional applications.

Use of the Substrates and Probes of the Invention to Stain Samples

The dyes of the invention are only partially protonated at neutral physiological pH values. By careful selection of the substituents on the substrate, the spectral properties of the probe can be tuned over a wide range of the visible and near infra-red spectrum, making them especially useful for multicolor applications. Similarly, careful selection of substituents allow the pH selectivity of the dyes of the invention to be tuned for specific applications. For example, a dye having a pKa that is less basic will be less protonated under more acidic conditions in the cell, and therefore more selectively be detected at locations having a lower pH.

The preferred substrates of the present invention are freely permeant to cell membranes, and selectively accumulate in the target organelles based upon the described intracellular targeting mechanisms. In addition, the peptide targeting groups of the present invention are known to be actively transported across the plasma membrane of mammalian cells by the process of retrograde transport [Eward H. W. Pap, Tobias B. Dansen, Ruben van Summeren & Karel W. A. Wirtz (2001) Experimental Cell Research 265: 288-293; Johannes L, Tenza D, Antony C, Goud B, (1997) J. Biol. Chem. 272: 19554-19561; Majoul I V, Bastiaens P I, Söling HD (1996) J. Cell Biol. 133(4):777-789.]

The staining characteristics of the preferred substrates are generally not reversed or are only partially reversed by subsequent treatment of the cells with additional cell-permeant compounds. In some cases, the staining is preserved even after fixation and/or permeabilization of the cells. The examples indicate the permanence of the staining parameters available to the practitioner practicing the invention.

The probes of the present invention are utilized by preparing a labeling solution containing one or more of the dyes of the present application, introducing the labeling solution into the sample containing or thought to contain the specific organelle and enzyme(s), incubating the sample for a time sufficient to produce a detectable fluorescent staining pattern, and observing or analyzing the staining pattern in the sample. The sample may be a cell or cells that contain organelles or the sample may contain isolated organelles (i.e. not incorporated in a cell), or the sample may be two solutions separated by a semi-permeable membrane.

The degree of staining of the organelles is a reflection of the enzyme activity in the organelle at the time of staining, i.e., the degree of staining is indicative of whether or not the organelle contains the enzyme at the time of staining, the amount of enzyme that is present, and the performance of the enzyme (enzyme function) as well as the length of the labeling time (enzyme kinetics). The analysis of mutations in enzymes due to genetic diseases is a specific embodiment of the present invention. While the dyes of the present invention are typically used for staining the organelles of live cells, the present invention is also useful for staining isolated (i.e. cell-free) organelles, provided the organelles are not disrupted and the enzyme still exists and is active in the isolated organelle or in the medium in which it is suspended. While in general the presence of organelles can be considered an indicator of cell viability, it is possible to render a cell non-viable, while still retaining organelles in the sample (cell fixation). The substrates of the present invention may also be useful in the analysis of enzyme activity when staining is followed by lysis of the cell and analysis of the fluorescent or chromogenic signal using standard techniques (e.g. fluorescence microtiterplate reader, fluorometers, UV/Vis spectrometer).

Furthermore, the substrates of the present invention can be made from fluorescent dyes that have the property of modifying their fluorescence spectrum as a function of pH upon enzyme turnover. Among the reporter dyes that exhibit changes in signal dependent upon the pH environment at the site of activity are the courmarins, fluoresceins, naphthfluoresceins, carbocyanines and rhodamines.

Preparation of a Labeling Solution

The pure substrates may have limited solubility in water at high concentrations. Typically a stock solution is prepared by dissolving a known mass of the pure substrate in an organic solvent and then diluting this stock solution with buffer or media for live cell analysis. Preferred organic solvents for preparation of the stock solutions are DMSO, DMF, N-methylpyrrolidone, acetone, acetonitrile, dioxane, tetrahydrofuran, methanol or ethanol or other completely water-miscible solvents. Alternatively, the substrate is dispersed in a water immiscible solvent or oil, or is evaporated from an organic solvent leaving a thin film. The stock solutions should be protected from light at all times due to the potential for photobleaching, common for fluorophores. The labeling solution is prepared by diluting an aliquot of the stock solution into an aqueous or partially aqueous buffer or into media or plasma to the desired labeling concentration. In one embodiment of the invention, two or more dyes of the invention are present in the labeling solution, having distinct spectral properties, which can be monitored simultaneously (providing multiplexed analysis).

In general the amount of substrate added in the labeling solution is the minimum amount required to yield detectable staining of the target organelles present in the sample within a reasonable time, with minimal background fluorescence or staining of other organelles or cellular structures. The amount of substrate required for staining eukaryotic cells depends on the sensitivity required for staining the intracellular organelles, the number of cells present, the permeability of the cell membrane to the substrate, and the time required for the probe to localize to the organelles and present a detectable signal. The required concentration for the labeling solution is determined by systematic variation in labeling concentration until a satisfactory fluorescent labeling is accomplished. Typically, the amount of substrate required for staining animal cells is 1 to 100 uM, preferably below 500 uM.

In addition, since the enzyme assays are kinetic in nature, the length of time used for staining can provide a method of adjusting differential staining parameters. Low concentrations of dye require longer incubation times for equivalent fluorescent brightness to be reached. Typically cells incubated in 10 uM labeling solution require about 1 hour to attain an arbitrary level of fluorescent staining that is reached in about 15 minutes using a 200 uM labeling solution. Monitoring the staining over these incubation times can be used to monitor kinetic parameters of the enzyme or enzymes being interrogated. For those embodiments where the organelles to be stained are present in plant cells, yeast or other fungal cells, a higher concentration of dye is typically used, due to the lower permeability of the plant, yeast or fungal cell membranes. Typically, when staining fungal cells, a dye concentration of 1 mM is satisfactory to give good staining results.

Staining concentrations less than about 100 uM give good staining of organelles in live animal cells. At higher concentrations of stain, background fluorescence increases in live cells, but resolution of acidic organelles after fixation is improved. Staining of isolated (cell-free) organelles typically requires lower concentrations of substrates.

The exact concentration of substrates to be used is dependent upon the experimental conditions and the desired results and optimization of experimental conditions is required to determine the best concentration of stain and duration of incubation to be used in a given application.

Sample Types

The sample optionally comprises cell-free isolated organelles or cells that contain the target organelles. Any cells that contain the desired organelles can be used, including but not limited to, fresh or cultured cells, cell lines, cells in biological fluids, cells in tissue or biopsy samples, yeast cells, fungal cells, plant cells and sperm cells. Where the sample contains cells, the cells are optionally abnormal cells, such as tumor cells or other cancer cells, where the abnormal cells are present in vitro or in vivo, or primary cells derived from patients with specific disease. Target organelles of interest that are stained using the present method of staining include, but are not limited to, the Endoplasmic Reticulum, the cis- and trans-Golgi Apparatus, Secretory Protein Trafficking Vesicles, tubulovesicular transport intermediates, intracellular membrane transport structures or the like. In one embodiment of the invention, the staining method is used to label multiple organelles in the same sample. Typically, the organelles that are stained are the ER and Golgi apparatus.

In addition, certain bacterial species including, but not limited to, *Legionella pneumophila, Brucella, Cholera, Chlamydia* or malarial infections, are known to sequester within individual organelles in living mammalian cells [Celli J, Tsolis R M (2015) "Bacteria, the endoplasmic reticulum and the unfolded protein response: friends or foes?" Nature Reviews Microbiology 13:71-82.]. The substrates of the present invention are also useful in detection of enzymes produced by these infecting bacteria and may also find utility in the analysis or diagnosis of bacterial or viral disease infecting living mammalian cells.

Staining the Sample

The sample is typically stained by passive means; that is the labeling solution is combined with the sample being analyzed and incubated for a length of time. The substrates of the present invention are introduced into the sample organelles by incubation of the sample in the labeling solution. Where the sample contains a cell or cells, the cells are similarly stained by incubation of the cell or cells in the labeling solution, typically while the cells are being grown under standard sterile culture conditions. Alternatively, the sample is stained by direct uptake of the substrate from a thin film of the substrate applied to a plate, microplate or cell well, or by adhering the substrate to a latex bead or polymer matrix that is introduced into the sample. Any other method of introducing the substrates into the sample cell, such as microinjection of a labeling solution, can be used to accelerate introduction of the substrates into the cellular cytoplasm. Typically the substrates will be introduced into the sample cell by incubation in the labeling solution, or by microinjection. Preferably the substrate is introduced to the sample by incubation in the labeling solution for a fixed period of time. Microinjection of substrate solution is used when labeling of the organelles within a single cell is desired, within a colony of other complex arrangement of sample cells.

A number of reagents and conditions are known to affect the uptake of the substrates into the target organelles, and therefore affect the staining by the substrates of the invention, including but not limited to nutrients (for example carbohydrates such as glucose), surfactants and selected drugs that are also included herein by example.

The substrates of the present invention are generally non-toxic to the living cells and organelles being labeled. Sample cells have been incubated in a 200 uM substrate solution for 24 hours without observable changes in morphology, viability or other harmful effects. Stained cells have been observed to undergo normal cell division, producing daughter cells that also possess stained organelles.

Preparation for Observation

Optionally, the cells or isolated organelles are washed to improve the results of the staining procedure. Washing the sample cell or cells after incubation in the labeling solution, or optionally after fixation or permeabilization, can greatly improve the visualization of the stained organelles. This is largely due to the decrease in non-specific background fluorescence after washing. Satisfactory visualization of organelles is possible without washing by using low labeling concentrations (for example <10 uM).

The sample can be observed immediately after staining of the organelles becomes evident. After staining, the cells or isolated organelles in a sample are optionally fixed with common reagents known in the art. Selected embodiments of the substrates described above are well retained in cells, and sample cells stained with these substrates retain considerable fluorescent staining after fixation. A number of fixatives and fixation conditions are suitable for practicing this invention. Useful fixatives include, but are not limited to, formaldehyde, paraformaldehyde, formalin, glutaraldehyde, cold methanol and 3:1 methanol acetic acid. Typically, cell fixation is accomplished by incubating the stained cells in a 3.7% solution of paraformaldehyde for about 15-30 minutes. Fixation is typically used to preserve cellular morphology and to reduce biohazards when working with pathogenic samples.

Fixation is optionally followed or accompanied by permeabilization, such as with acetone, ethanol, DMSO or various detergents. Permeabilization is utilized to allow bulky additional detection reagents such as labeled antibodies to enter the cellular space that would ordinarily be impermeant to an intact cellular membrane. A large variety of fixatives, fixation conditions, and permeabilization agents are known in the art, and other methods of fixing or permeabilizing sample cells in conjunction with the stains of the present invention will be obvious to one of ordinary skill.

The use of antifade mountants for increased signal intensity and minimized photobleaching or imaging buffers formulated to lower background fluorescence, maintain proper pH and osmolarity during long duration staining at 37°, provide an energy source and preserve fluorescent signals are compatable with staining using the substrates of the present invention and can be incorporated into staining protocols without affecting results.

Additional Detection Reagents

The use of the organelle stains of the present invention is optionally combined with the use of an additional detection reagent. An additional detection reagent is a reagent that produces a detectable response due to the presence of a specific cell component, intracellular substance, or cellular condition. One or more additional detection reagents may be used in conjunction with the stains of the present invention, before or after fixation and/or permeabilization. The additional detection reagent may be used to stain the entire cell, or a cellular substructure. The fluorescent signal of the organelle stains of the present invention and the detectable response of the additional detection reagent may be observed simultaneously or sequentially. The observation of organellar staining and a detectable response that are spatially coincident indicate that the additional detection reagent is associated with the target organelles. A variety of measurements can be made within organelles in this manner, even when the additional detection reagent does not itself localize selectively within the target organelles.

One class of appropriate additional detection reagents are fluorescent nucleic acid stains. A wide variety of appropriate nucleic acid stains are known in the art, including but not limited to, Thiazole Orange, ethidium homodimer, propidium iodide, Hoechst 33342, and DAPI. Additional useful nucleic acid stains are described in WO 93/06482; U.S. Pat. Nos. 5,436,134; 5,321,130; 5,410,030; and 5,437,980. The use of an appropriate nucleic acid stain in conjunction with the dyes of the present invention can be selected to allow simultaneous observation of the target organelles in conjunction with nuclear DNA, cellular RNA and/or mitochondrial DNA. Of particular utility is an additional detection reagent that is a cell-permeant nucleic acid stain, such as those described in U.S. Pat. No. 5,436,134, allowing simultaneous visualization of acidic organelles and the cell nucleus. Use of these additional nucleic acid stains in conjunction with the organelle stains of the present invention provide a direct means of counting the number of cells present in a specific sample, since there is typically only one nucleus per cell. In this manner the number of stained organelles per cell can also be calculated as well as the relative intensity of the organelles per individual cell or between different cell types. This data can be used to indicate the level of enzyme activity per cell or between different individual cells.

Other appropriate additional detection reagents include selected fluorescent metal ion indicators described in U.S. Pat. Nos. 5,453,517 and 5,405,975.

In another embodiment of the invention, an appropriate additional detection reagent is any probe that selectively stains a cellular organelle such as the cell membrane, nucleus, lysosome, and mitochondrion or is a second organelle probe for the same organelle or for the ER or Golgi apparatus.

Specific examples of additional detection reagents include mitochondria-targeted stains, such as Rhodamine 123. Additional fluorescent stains specific for mitochondria are described in U.S. Pat. No. 5,459,268. The above mitochondrial stains accumulate in mitochondria, and are fixable therein, allowing simultaneous visualization of both mitochondria and the ER or Golgi organelles in fixed and permeabilized cells. Additional lysosomal stains are described in U.S. Pat. No. 8,460,862.

In one embodiment, the additional detection reagent comprises: a) one member of a specific binding pair or a series of specific binding pairs, and b) a means for producing a detectable response. A specific binding pair member can be a ligand or a receptor. As used in this document, the term ligand means any organic compound for which a receptor naturally exists or can be prepared. A receptor is any compound or composition capable or recognizing a spatial or polar organization of a molecule, e.g. epitopic or determinant site. Ligands for which naturally occurring receptors exist include natural and synthetic peptides and proteins, including avidin and streptavidin, antibodies, enzymes, and hormones; nucleotides and natural or synthetic oligonucleotides; lipids; polysaccharides and carbohydrates; lectins; and a variety of drugs, including therapeutic drugs and drugs of abuse and pesticides. Ligands and receptors are complementary members of a specific binding pair, each specific binding pair member having an area on the surface or in a cavity which specifically binds to and is complementary with a particular spatial and polar organization of the other.

The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. In one embodiment, the additional detection reaction comprises an enzyme substrate to produces a fluorescent precipitate in the presence of the appropriate enzyme, as described in U.S. Pat. Nos. 5,316,906 and 5,443,986.

In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a "complementary conjugate". Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

The additional detection reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a cell sample. Such detectable responses include the change in, or appearance of, color, fluorescence, reflectance, pH, chemiluminescence, infrared emission, or the deposition of an electron-rich substrate. Appropriate labels to provide a detectable response include, but are not limited to, a visible or fluorescent dye, an enzyme substrate which produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine).

Observation

At any time after or during staining, the sample is illuminated with a wavelength of light that results in a detectable fluorescence response, and subsequently observed with a means for detecting the detectable response of fluorescent labeled organelles, if present. In one embodiment of the invention, the fluorescently labeled organelles are observed after the cell or cells have additionally been fixed and/or permeabilized. Observation is accomplished using visible light microscopy, or alternatively, observation of the sample comprises illuminating the stained sample with a wavelength of light appropriate to generate a fluorescent response, and visually examining the sample by use of a microscope, or confocal microscope.

The sample is optionally illuminated at a wavelength of ultraviolet, visible or infrared light specific for optimal excitation of the fluorophore dye present in the sample after enzyme action to remove the BLOCK group. Where the sample contains more than one BLOCK, or contains an additional detection reagent, illumination occurs at a wavelength that generates a detectable fluorescence response in each fluorescent dye or additional detection reagent, where said dyes and detection reagents possess overlapping excitation maxima.

Typically, the dyes of the invention typically possess a strong absorbance at visible wavelengths, typically at greater than 450 nm, preferably at greater than 500 nm, yet more preferably at greater than 600 nm. The preferred dyes of the invention exhibit an extinction coefficient greater than 10,000/cm M, preferably at greater than 30,000/cm M. The fluorophores of the invention typically possess quantum yields of fluorescence emission that are greater than 0.3, preferably greater than 0.7.

Optionally, the sample is observed using instrumentation. For example, where the sample contains a cell or cells, observation of the sample is accomplished by illuminating the stained cell or cells with a wavelength of light appropriate to generate a fluorescent response, and electronically detecting and optionally quantifying the fluorescent emission of the stained organelles using an appropriate instrument, such as a fluorescence microscop, a digital camera, a fluorometer, a fluorescent microplate reader, or a flow cytometer. These instruments routinely contain specific filters to reduce incident or extraneious light wavelengths but allow the emitted light to be interrogated.

The observation of the fluorescent response of the sample optionally includes selecting or sorting the stained organelles in cells based upon their fluorescent response. Typically the sample comprises cells having stained organelles, and the cells of the sample are sorted based upon the overall staining of the individual cells. The step of sorting is typically accomplished using a flow Cytometer, fluorescence activated cell sorter or a suitably equipped fluorescence microscope.

Photodynamic Therapy

The use of simple fluorescent dyes as sensitizing agents to enhance photodynamic therapy (PDT) has been described in U.S. Pat. Nos. 5,189,029 and 5,446,157. Photodynamic therapy refers to the process wherein illumination is utilized to destroy cells, typically abnormal cells, that have previously been labeled with a dye. Several references, including Geze, et al. (Photochem. Photobiol. 20, 23-35 (1993); and Berg et al. (Int. J. Cancer 59, 814-822 (1994) have previously indicated that the photolysis of dyes that are localized to lysosomes destroys tumor cells. Furthermore, the lysosomes of tumor cells are generally considered to have a lower pH than normal lysosomes. Selective uptake of PDT dyes into tumor cells in preference to normal cells is an important property allows selective photodestruction of abnormal cells in the course of PDT treatment, while minimizing the destruction of normal cells.

The method of the current invention has utility for photodynamic therapy, as described above, as the greater activity of enzymes in the organelles of tumor cells will result in greater uptake of the targeted substrates into tumor cells. Photolysis of the stained cells will then result in destruction of the target tumor cells without affecting neighboring normal cells and tissues. Although cells and tissues stained according to the present method are potential PDT targets, preferably the long wavelength fluorescent dyes used for PDT targeting of cells are those that absorb beyond 600 nm, more preferably those that absorb beyond 650 nm, due to the enhanced penetration of light through tissues at these wavelengths. Particularly preferred are the dyes of the invention having fused aromatic substituents that are further substituted by a LINK-T moiety. Additional preferred dyes of the invention for PDT are those having bromine or iodine substituents such as eosin and erythrosine.

Preferred dye concentrations for labeling cells for PDT are those concentrations that have been determined to produce the greatest selective uptake of dye into abnormal cells without detriment to normal cells, such that photolytic activity is maintained in the abnormal cells. As described above, micromolar concentrations of dye are effective in staining specific organelles of live cells. The dyes are applied to cells for PDT by means well understood in the art, including local or systemic injection, topical application, incorporation into liposomes or other means. Dye uptake into cells is by passive diffusion or receptor-mediated uptake. Selective accumulation in the ER or Golgi is facilitated by the process of retrograde transport. Photolysis is performed with any excitation source that is capable of producing light that can be absorbed by the dye, including lasers and light sources that produce near-infrared or infrared irradiation. This light may be delivered either directly to the cells that contain the dye, or delivered indirectly such as through an optical fiber. Fluorescence properties of the dye can be used to guide and determine which cells are to be irradiated.

As described herein, targeted substrates of the present invention may be used with high-throughput screening systems to quickly and accurately assess the effect of gene regulation or secondary drug application on organelle (Golgi, peroxisome, nulear or ER) enzyme function. No prior attempt has been made to utilize the described combination of enzyme substrate targeting to the specific organelles such as the Golgi or ER with specific organelle enzyme activity detection in living cells.

The instant systems are useful for specific medical applications. In particular, the targeted substrates shown to be effective for monitoring enzymes in live cells representing disease can be used in existing high content drug screening systems, for the analysis of physiological conditions known to influence organelle (Golgi, E R, etc.) enzymes and for the identification and validation of treatment modalities that are either existing or under development. In addition, use of the instant reagents and methods and allied protocols in combination with other detection modalities in vivo, will provide tools for general analysis by the pharmaceutical and general biology research communities for use in monitoring new systems, especially in neurodegenerative diseases research. The resulting tools will have wide applications for the analysis of and selection for cell types or cells with various levels of enzyme activity by methods such as Flow Cytometry and Fluorescence Activated Cell sorting (FACS). Finally, the instant reagents and methods will find application to the diagnosis of disease.

The therapeutic options for treating many of the diseases affecting the ER and Golgi are relatively limited; in fact, there are currently no available therapies for many of these disorders. The problem is further compounded by difficulties in delivering therapeutic agents to the central nervous system, which is where the pathology is frequently manifested and monitoring the effectiveness of treatment regimens is problematic. To date, therapeutic efforts have mainly focused on strategies for augmenting enzyme concentrations to compensate for the underlying defect. These strategies include allogenic bone-marrow transplantation, enzyme-replacement therapy, substrate deprivation, gene therapy or progenitor cell infusion. The instant sensitive and specific assays for monitoring organelle enzyme activities in living cells will be of significant value in monitoring the success of current therapies and for discovery of new therapeutic strategies for diseases of specific organelle origin.

The organelle stains and substrates of this invention are further designed to allow free permeation through the plasma and organelle membranes of intact cells and can be used for staining cells at very low concentrations necessary for high-content screening and analysis. Further, they are non-toxic to living cells or tissues. The instant dyes, substrates and methods are also useful for investigating the biogenesis of organelles, the development of autophagic vacuoles, secretory mechanisms, investigating retina and cultured neurons, monitoring changes in organelle enzyme activities, evaluating the relative levels of enzymes in both normal and diseased states and detecting pH or ion gradients within the targeted organelles. The current invention is also useful for labeling specific phenotypic cell types that possess these organelles, including mammalian, bacterial, yeast, spermatozoa and plant cells, and may provide new methods of characterizing infectious or invasive species.

Among the enzymes that are present in these organelles and that can be detected using the substrates of the present invention are those listed in Table 11 (Golgi Enzymes) and Table 12 (Endoplasmic Reticulum Enzymes) below given as a descriptive embodiment of the present invention but not intended to be a complete list of possible enzyme activities which may be detected using the substrates and methods of the present invention. Other enzymes which may be detected using the systems and substrates of the present invention will be obvious to a person skilled in the art.

TABLE 11

List of Golgi Enzymes (EC Number)

protein-lysine 6-oxidase (1.4.3.13)
NADPH-hemoprotein reductase (1.6.2.4)
dihydrolipoyl dehydrogenase (1.8.1.4)
thiol oxidase (1.8.3.2)
glutathione peroxidase (1.11.1.9)
4-hydroxyphenylpyruvate dioxygenase (1.13.11.27)
procollagen-proline dioxygenase (1.14.11.2)
trans-cinnamate 4-monooxygenase (1.14.13.11)
sterol-14-alpha-demethylase(1.14.13.70)
tryptophan 5-monooxygenase(1.14.16.4)
cholesterol 25-hydroxylase (1.14.99.38)
phosphoethanolamine N-methyltransferase (2.1.1.103)
[phosphatase 2A protein]-leucine-carboxy methyltransferase (2.1.1.233)
glutamate formimidoyltransferase (2.1.2.5)
N-acetylneuraminate 7-O(or 9-O)-acetyltransferase (2.3.1.45)
peptide alpha-N-acetyltransferase (2.3.1.88)
glutaminyl-peptide cyclotransferase (2.3.2.5)
cellulose synthase (UDP-forming) (2.4.1.12)

TABLE 11-continued

List of Golgi Enzymes (EC Number)

chitin synthase (2.4.1.16)
lactose synthase (2.4.1.22)
beta-N-acetylglucosaminylglycopeptide beta-1 (2.4.1.38)
polypeptide N-acetylgalactosaminyltransferase (2.4.1.41)
polygalacturonate 4-alpha-galacturonosyltransferase (2.4.1.43)
ganglioside galactosyltransferase (2.4.1.62)
3-galactosyl-N-acetylglucosaminide 4-alpha-L-fucosyltransferase (2.4.1.65)
procollagen glucosyltransferase (2.4.1.66)
glycoprotein 6-alpha-L-fucosyltransferase (2.4.1.68)
galactoside 2-alpha-L-fucosyltransferase (2.4.1.69)
ceramide glucosyltransferase (2.4.1.80)
N-acetyllactosamine synthase (2.4.1.90)
(N-acetylneuraminyl)-galactosylglucosylceramide N-acetylgalactosaminyltransferase (2.4.1.92)
glycoprotein-N-acetylgalactosamine 3-beta-galactosyltransferase (2.4.1.122)
GDP-Man:Man1GlcNAc2-PP-dolichol alpha-1,3-mannosyltransferase (2.4.1.132)
xylosylprotein 4-beta-galactosyltransferase (2.4.1.133)
galactosylxylosylprotein 3-beta-galactosyltransferase (2.4.1.134)
alpha-1,6-mannosyl-glycoprotein 2-beta-N-acetylglucosaminyltransferase (2.4.1.143)
beta-1,4-mannosyl-glycoprotein 4-beta-N-acetylglucosaminyltransferase (2.4.1.144)
acetylgalactosaminyl-O-glycosyl-glycoprotein beta-1 (2.4.1.147)
acetylgalactosaminyl-O-glycosyl-glycoprotein beta-1 (2.4.1.148)
N-acetyllactosaminide beta-1-beta-1,3-galactosyltransferase (2.4.1.149)
4-galactosyl-N-acetylglucosaminide 3-alpha-L-fucosyltransferase (2.4.1.152)
alpha-1,6-mannosyl-glycoprotein 6-beta-N-acetylglucosaminyltransferase (2.4.1.155)
sterol-3-beta-glucosyltransferase (2.4.1.173)
glucuronosyl-N-acetylgalactosaminyl-proteoglycan 4-beta-N-acetylgalactosaminyltransferase (2.4.1.175)
lactosylceramide beta-1,3-galactosyltransferase (2.4.1.179)
lactosylceramide 1 (2.4.1.206)
hyaluronan synthase (2.4.1.212)
glycoprotein 3-alpha-L-fucosyltransferase (2.4.1.214)
peptide-O-fucosyltransferase (2.4.1.221)
O-fucosylpeptide 3-beta-N-acetylglucosaminyltransferase (2.4.1.222)
glucuronyl-galactosyl-proteoglycan 4-alpha-N-acetylglucosaminyltransferase (2.4.1.223)
glucuronosyl-N-acetylglucosaminyl-proteoglycan 4-alpha-N-acetylglucosaminyltransferase (2.4.1.224)
N-acetylglucosaminyl-proteoglycan 4-beta-glucuronosyltransferase (2.4.1.225)

TABLE 11-continued

List of Golgi Enzymes (EC Number)

N-acetylgalactosaminyl-proteoglycan 3-beta-glucuronosyltransferase (2.4.1.226)
initiation-specific alpha-1 (2.4.1.232)
N-acetyl-beta-glucosaminyl-glycoprotein 4-beta-N-acetylgalactosaminyltransferase (2.4.1.244)
glucosylceramide beta-1,4-galactosyltransferase (2.4.1.274)
1,4-beta-D-xylan synthase (2.4.2.24)
protein xylosyltransferase (2.4.2.26)
glycoprotein 2-beta-D-xylosyltransferase (2.4.2.38)
xyloglucan 6-xylosyltransferase (2.4.2.39)
xylogalacturonan beta-1,3-xylosyltransferase (2.4.2.41)
beta-galactoside alpha-2,6-sialyltransferase 2.4.99.1 ( )
monosialoganglioside sialyltransferase (2.4.99.2)
beta-galactoside alpha-2-alpha-2,3-sialyltransferase (2.4.99.4)
alpha-N-acetylneuraminate alpha-2,8-sialyltransferase (2.4.99.8)
lactosylceramide alpha-2,3-sialyltransferase (2.4.99.9)
N-acylmannosamine kinase (2.7.1.60)
1-phosphatidylinositol 4-kinase (2.7.1.67)
1-phosphatidylinositol-4-phosphate 5-kinase (2.7.1.68)
sphinganine kinase (2.7.1.91)
diacylglycerol kinase (ATP dependent) (2.7.1.107)
ceramide kinase (2.7.1.138)
1-phosphatidylinositol-5-phosphate 4-kinase (2.7.1.149)
nicotinamide-nucleotide adenylyltransferase (2.7.7.1)
UTP-glucose-1-phosphate uridylyltransferase (2.7.7.9)
nicotinate-nucleotide adenylyltransferase (2.7.7.18)
N-acylneuraminate cytidylyltransferase (2.7.7.43)
diacylglycerol cholinephosphotransferase (2.7.8.2)
ceramide cholinephosphotransferase (2.7.8.3)
CDP-diacylglycerol-inositol 3-phosphatidyltransferase (2.7.8.11)
UDP-N-acetylglucosamine-lysosomal-enzyme N-acetylglucosaminephosphotransferase (2.7.8.17)
sphingomyelin synthase (2.7.8.27)
non-specific serine/threonine protein kinase (2.7.11.1)
Goodpasture-antigen-binding protein kinase (2.7.11.9)
cAMP-dependent protein kinase (2.7.11.11)
protein kinase C (2.7.11.13)
polo kinase (2.7.11.21)
cyclin-dependent kinase (2.7.11.22)
mitogen-activated protein kinase (2.7.11.24)
mitogen-activated protein kinase kinase (2.7.11.25)
chondroitin 4-sulfotransferase (2.8.2.5)
[heparan sulfate]-glucosamine N-sulfotransferase (2.8.2.8)
galactosylceramide sulfotransferase (2.8.2.11)
steroid sulfotransferase (2.8.2.15)
chondroitin 6-sulfotransferase (2.8.2.17)
protein-tyrosine sulfotransferase (2.8.2.20)
[heparan sulfate]-glucosamine 3-sulfotransferase 3 (2.8.2.30)
N-acetylgalactosamine 4-sulfate 6-O-sulfotransferase (2.8.2.33)
phosphatidylinositol deacylase (3.1.1.52)
alkaline phosphatase (3.1.3.1)
acid phosphatase (3.1.3.2)
phosphatidate phosphatase (3.1.3.4)
phosphatidylinositol-4-phosphate phosphatase (3.1.3.B4)
5'-nucleotidase (3.1.3.5)
3'(2'),5'-bisphosphate nucleotidase (3.1.3.7)
glycerol-2-phosphatase (3.1.3.19)
nucleotidase (3.1.3.31)
phosphoinositide 5-phosphatase (3.1.3.36)
protein-tyrosine-phosphatase (3.1.3.48)
phospholipase C (3.1.4.3)
phospholipase D (3.1.4.4)
sphingomyelin phosphodiesterase (3.1.4.12)
glycerophosphoinositol glycerophosphodiesterase (3.1.4.44)
N-acetylglucosamine-1-phosphodiester alpha-N-acetylglucosaminidase (3.1.4.45)
glycosylphosphatidylinositol phospholipase D (3.1.4.50)
3',5'-cyclic-AMP phosphodiesterase (3.1.4.53)
oligo-1,6-glucosidase (3.2.1.10)
exo-alpha-sialidase (3.2.1.18)
alpha-mannosidase (3.2.1.24)
beta-fructofuranosidase (3.2.1.26)
alpha-L-fucosidase (3.2.1.51)
glycosylceramidase (3.2.1.62)
glucan 1,3-alpha-glucosidase (3.2.1.84)
mannosyl-oligosaccharide 1,2-alpha-mannosidase (3.2.1.113)
mannosyl-oligosaccharide 1,3-1,6-alpha-mannosidase (3.2.1.114)
glycoprotein endo-alpha-1,2-mannosidase (3.2.1.130)
poly(ADP-ribose) glycohydrolase (3.2.1.143)
microsomal epoxide hydrolase (3.3.2.9)
soluble epoxide hydrolase (3.3.2.10)
cholesterol-5,6-oxide hydrolase (3.3.2.11)
membrane alanyl aminopeptidase (3.4.11.2)
cystinyl aminopeptidase (3.4.11.3)
aminopeptidase B (3.4.11.6)
dipeptidyl-peptidase IV (3.4.14.5)
carboxypeptidase C (3.4.16.5)
carboxypeptidase D (3.4.16.6)
metallocarboxypeptidase D (3.4.17.22)
cathepsin X (3.4.18.1)
Duodenase (3.4.21.B3)
prolyl oligopeptidase (3.4.21.26)
proprotein convertase 5 (3.4.21.B26)
proprotein convertase 7 (3.4.21.B27)
tissue kallikrein (3.4.21.35)
Hippostasin (3.4.21.B42)
Kexin (3.4.21.61)
Furin (3.4.21.75)
Proprotein convertase 1 (3.4.21.93)
rhomboid protease (3.4.21.105)
site-1 protease (3.4.21.112)
Oviductin (3.4.21.120)
calpain 8 (3.4.22.B28)

TABLE 11-continued

List of Golgi Enzymes (EC Number)

bleomycin hydrolase (3.4.22.40)
caspase-2 (3.4.22.55)
cathepsin D (3.4.23.5)
cathepsin E (3.4.23.34)
memapsin 1 (3.4.23.45)
memapsin 2 (3.4.23.46)
ADAMTS5 endopeptidase (3.4.24.B12)
PHEX peptidase (3.4.24.B15)
ADAM19 (3.4.24.B27)
endothelin-converting enzyme 1 (3.4.24.71)
ADAM10 endopeptidase (3.4.24.81)
S2P endopeptidase (3.4.24.85)
ADAM 17 endopeptidase (3.4.24.86)
ADAMTS13 endopeptidase (3.4.24.87)
Ceramidase (3.5.1.23)
allantoate deiminase (3.5.3.9)
adenosinetriphosphatase (3.6.1.3)
nucleoside diphosphate phosphatase (3.6.1.6)
thiamine-triphosphatase (3.6.1.28)
guanosine-diphosphatase (3.6.1.42)
phospholipid-translocating ATPase (3.6.3.1)
Cu2+-exporting ATPase (3.6.3.4)
Ca2+-transporting ATPase (3.6.3.8)
H+/K+-exchanging ATPase (3.6.3.10)
alpha-factor-transporting ATPase (3.6.3.48)
microtubule-severing ATPase (3.6.4.3)
plus-end-directed kinesin ATPase (3.6.4.4)
vesicle-fusing ATPase (3.6.4.6)
heterotrimeric G-protein GTPase (3.6.5.1)
small monomeric GTPase (3.6.5.2)
dynamin GTPase (3.6.5.5)
UDP-glucuronate decarboxylase (4.1.1.35)
phosphatidylserine decarboxylase (4.1.1.65)
formimidoyltetrahydrofolate cyclodeaminase (4.3.1.4)
phenylalanine ammonia-lyase (4.3.1.24)
UDP-glucose 4-epimerase (5.1.3.2)
UDP-N-acetylglucosamine 2-epimerase (non-hydrolysing) (5.1.3.14)
Prostaglandin-D synthase (5.3.99.2)

TABLE 12

List of Golgi Enzymes (EC Number)

glucuronate reductase (1.1.1.19)
hydroxymethylglutaryl-CoA reductase (NADPH) (1.1.1.34)
3-hydroxyacyl-CoA dehydrogenase (1.1.1.35)
acetoacetyl-CoA reductase (1.1.1.36)
11beta-hydroxysteroid dehydrogenase ((NAD+) (1.1.1.B40)
isocitrate dehydrogenase (NADP+) (1.1.1.42)
glucose 1-dehydrogenase [NAD(P)+] (1.1.1.47)
glucose-6-phosphate dehydrogenase (NADP+) (1.1.1.49)
3(or 17)beta-hydroxysteroid dehydrogenase (1.1.1.51)
3alpha(or 20beta)-hydroxysteroid dehydrogenase (1.1.1.53)
17beta-estradiol 17-dehydrogenase (1.1.1.62)

TABLE 12-continued

List of Golgi Enzymes (EC Number)

testosterone 17beta-dehydrogenase (NADP+) (1.1.1.64)
hydroxymethylglutaryl-CoA reductase (1.1.1.88)
3-oxoacyl-[acyl-carrier-protein] reductase (1.1.1.100)
3-dehydrosphinganine reductase (1.1.1.102)
all-trans-retinol dehydrogenase (NAD+) (1.1.1.105)
11beta-hydroxysteroid dehydrogenase (1.1.1.146)
21-hydroxysteroid dehydrogenase (NAD+) (1.1.1.150)
3beta-hydroxysteroid-4alpha-carboxylate 3-dehydrogenase (decarboxylating) (1.1.1.170)
carbonyl reductase (NADPH) (1.1.1.184)
prostaglandin-F synthase (1.1.1.188)
3beta-hydroxysteroid 3-dehydrogenase (1.1.1.270)
3beta-hydroxy-5alpha-steroid dehydrogenase (1.1.1.278)
NADP-retinol dehydrogenase (1.1.1.300)
11-cis-retinol dehydrogenase (1.1.1.315)
very-long-chain 3-oxoacyl-CoA reductase (1.1.1.330)
alcohol oxidase (1.1.3.13)
D-mannitol oxidase (1.1.3.40)
vitamin-K-epoxide reductase (warfarin-sensitive) (1.1.4.1)
vitamin-K-epoxide reductase (warfarin-insensitive) (1.1.4.2)
aminobutyraldehyde dehydrogenase (1.2.1.19)
alcohol-forming fatty acyl-CoA reductase (1.2.1.84)
dihydropyrimidine dehydrogenase (NADP+) (1.3.1.2)
acyl-CoA dehydrogenase (NADP+) (1.3.1.8)
7-dehydrocholesterol reductase (1.3.1.21)
3-oxo-5alpha-steroid 4-dehydrogenase (NADP+) (1.3.1.22)
phosphatidylcholine desaturase (1.3.1.35)
DELTA14-sterol reductase (1.3.1.70)
DELTA24(241)-sterol reductase (1.3.1.71)
DELTA24-sterol reductase (1.3.1.72)
tRNA-dihydrouridine20 synthase [NAD(P)+] (1.3.1.91)
very-long-chain enoyl-CoA reductase (1.3.1.93)
secologanin synthase (1.3.3.9)
all-trans-retinol 13,14-reductase (1.3.99.23)
glutamate dehydrogenase [NAD(P)+] (1.4.1.3)
protein-lysine 6-oxidase (1.4.3.13)
cytochrome-b5 reductase (1.6.2.2)
NADPH-hemoprotein reductase (1.6.2.4)
NAD(P)H oxidase (H2O2-forming) (1.6.3.1)
glutathione reductase (NADPH) (1.6.4.2)
NAD(P)H dehydrogenase (quinone) (1.6.5.2)
monodehydroascorbate reductase (NADH) (1.6.5.4)
azobenzene reductase (1.7.1.6)
protein-disulfide reductase (1.8.1.8)
thiol oxidase (1.8.3.2)
protein-disulfide reductase (glutathione) (1.8.4.2)
peptide-methionine (R)—S-oxide reductase (1.8.4.12)
dimethylsulfoxide reductase (1.8.5.3)
iodide peroxidase (1.11.1.8)
glutathione peroxidase (1.11.1.9)
L-ascorbate peroxidase (1.11.1.11)
Peroxiredoxin (1.11.1.15)

TABLE 12-continued

List of Golgi Enzymes (EC Number)

prostamide/prostaglandin F2alpha synthase (1.11.1.20)
4-hydroxyphenylpyruvate dioxygenase (1.13.11.27)
Renilla-luciferin 2-monooxygenase (1.13.12.5)
procollagen-proline dioxygenase (1.14.11.2)
procollagen-lysine 5-dioxygenase (1.14.11.4)
procollagen-proline 3-dioxygenase (1.14.11.7)
peptide-aspartate beta-dioxygenase (1.14.11.16)
proline 3-hydroxylase (1.14.11.28)
flavin-containing monooxygenase (1.14.13.8)
trans-cinnamate 4-monooxygenase (1.14.13.11)
phosphatidylcholine 12-monooxygenase (1.14.13.26)
albendazole monooxygenase (1.14.13.32)
nitric-oxide synthase (NADPH dependent) (1.14.13.39)
(S)-limonene 3-monooxygenase (1.14.13.47)
(S)-limonene 6-monooxygenase (1.14.13.48)
isoflavone 3'-hydroxylase (1.14.13.52)
sterol 14alpha-demethylase (1.14.13.70)
N-methylcoclaurine 3'-monooxygenase (1.14.13.71)
methylsterol monooxygenase (1.14.13.72)
tabersonine 16-hydroxylase (1.14.13.73)
taxane 10beta-hydroxylase (1.14.13.76)
taxane 13alpha-hydroxylase (1.14.13.77)
ent-kaurene oxidase (1.14.13.78)
glyceollin synthase (1.14.13.85)
isoflavone 2'-hydroxylase (1.14.13.89)
cholesterol 24-hydroxylase (1.14.13.98)
25-hydroxycholesterol 7alpha-hydroxylase (1.14.13.100)
psoralen synthase (1.14.13.102)
8-dimethylallylnaringenin 2'-hydroxylase (1.14.13.103)
abieta-7 (1.14.13.109)
squalene monooxygenase (1.14.13.132)
unspecific monooxygenase (1.14.14.1)
alkane 1-monooxygenase (1.14.15.3)
tryptophan 5-monooxygenase (1.14.16.4)
alkylglycerol monooxygenase (1.14.16.5)
CMP-N-acetylneuraminate monooxygenase (1.14.18.2)
stearoyl-CoA 9-desaturase (1.14.19.1)
linoleoyl-CoA desaturase (1.14.19.3)
DELTA12-fatty-acid desaturase (1.14.19.6)
prostaglandin-endoperoxide synthase (1.14.99.1)
heme oxygenase (biliverdin-producing) (1.14.99.3)
steroid 17alpha-monooxygenase (1.14.99.9)
progesterone 11alpha-monooxygenase (1.14.99.14)
deoxyhypusine monooxygenase (1.14.99.29)
DELTA12-fatty acid dehydrogenase (1.14.99.33)
cholesterol 25-hydroxylase (1.14.99.38)
thyroxine 5'-deiodinase (1.97.1.10)
catechol O-methyltransferase (2.1.1.6)
phosphatidylethanolamine N-methyltransferase (2.1.1.17)
sterol 24-C-methyltransferase (2.1.1.41)
phosphatidyl-N-methylethanolamine N-methyltransferase (2.1.1.71)
protein-S-isoprenylcysteine O-methyltransferase (2.1.1.100)

TABLE 12-continued

List of Golgi Enzymes (EC Number)

isoflavone 7-O-methyltransferase (2.1.1.150)
aspartate carbamoyltransferase (2.1.3.2)
Transketolase (2.2.1.1)
carnitine O-acetyltransferase (2.3.1.7)
glycine N-acyltransferase (2.3.1.13)
glycerol-3-phosphate 1-O-acyltransferase (2.3.1.15)
aspartate N-acetyltransferase (2.3.1.17)
diacylglycerol O-acyltransferase (2.3.1.20)
carnitine O-palmitoyltransferase (2.3.1.21)
2-acylglycerol O-acyltransferase (2.3.1.22)
1-acylglycerophosphocholine O-acyltransferase (2.3.1.23)
sphingosine N-acyltransferase (2.3.1.24)
sterol O-acyltransferase (2.3.1.26)
lysine N-acetyltransferase (2.3.1.32)
beta-ketoacyl-[acyl-carrier-protein] synthase I (2.3.1.41)
glycerone-phosphate O-acyltransferase (2.3.1.42)
histone acetyltransferase (2.3.1.48)
serine C-palmitoyltransferase (2.3.1.50)
1-acylglycerol-3-phosphate O-acyltransferase (2.3.1.51)
naringenin-chalcone synthase (2.3.1.74)
long-chain-alcohol O-fatty-acyltransferase (2.3.1.75)
peptide alpha-N-acetyltransferase (2.3.1.88)
phosphatidylcholine-retinol O-acyltransferase (2.3.1.135)
carnitine O-octanoyltransferase (2.3.1.137)
glycoprotein O-fatty-acyltransferase (2.3.1.142)
phospholipid:diacylglycerol acyltransferase (2.3.1.158)
protein S-acyltransferase (2.3.1.225)
glutaminyl-peptide cyclotransferase (2.3.2.5)
ATP citrate synthase (2.3.3.8)
cellulose synthase (UDP-forming) (2.4.1.12)
glucuronosyltransferase (2.4.1.17)
lactose synthase (2.4.1.22)
1,3-beta-glucan synthase (2.4.1.34)
phenol beta-glucosyltransferase (2.4.1.35)
beta-N-acetylglucosaminylglycopeptide beta-1 (2.4.1.38)
polypeptide N-acetylgalactosaminyltransferase (2.4.1.41)
2-hydroxyacylsphingosine 1-beta-galactosyltransferase (2.4.1.45)
procollagen galactosyltransferase (2.4.1.50)
ganglioside galactosyltransferase (2.4.1.62)
3-galactosyl-N-acetylglucosaminide 4-alpha-L-fucosyltransferase (2.4.1.65)
procollagen glucosyltransferase (2.4.1.66)
ceramide glucosyltransferase (2.4.1.80)
dolichyl-phosphate beta-D-mannosyltransferase (2.4.1.83)
cyanohydrin beta-glucosyltransferase (2.4.1.85)
N-acetyllactosamine synthase (2.4.1.90)
protein N-acetylglucosaminyltransferase (2.4.1.94)
bilirubin-glucuronoside glucuronosyltransferase (2.4.1.95)
alpha-1,3-mannosyl-glycoprotein 2-beta-N-acetylglucosaminyltransferase (2.4.1.101)
dolichyl-phosphate-mannose-protein mannosyltransferase (2.4.1.109)
dolichyl-phosphate beta-glucosyltransferase (2.4.1.117)

TABLE 12-continued

List of Golgi Enzymes (EC Number)

glycoprotein-N-acetylgalactosamine 3-
beta-galactosyltransferase (2.4.1.122)
GDP-Man:Man3GlcNAc2-PP-dolichol
alpha-1,2-mannosyltransferase (2.4.1.131)
GDP-Man:Man1GlcNAc2-PP-dolichol
alpha-1,3-mannosyltransferase (2.4.1.132)
mannotetraose 2-alpha-N-
acetylglucosaminyltransferase (2.4.1.138)
N-acetylglucosaminyldiphosphodolichol N-
acetylglucosaminyltransferase (2.4.1.141)
chitobiosyldiphosphodolichol beta-
mannosyltransferase (2.4.1.142)
beta-1,4-mannosyl-glycoprotein 4-beta-N-
acetylglucosaminyltransferase (2.4.1.144)
glucuronosyl-N-acetylgalactosaminyl-
proteoglycan 4-beta-N-
acetylgalactosaminyltransferase
(2.4.1.175)
lactosylceramide beta-1,3-
galactosyltransferase (2.4.1.179)
phosphatidylinositol N-
acetylglucosaminyltransferase (2.4.1.198)
hyaluronan synthase (2.4.1.212)
peptide-O-fucosyltransferase (2.4.1.221)
glucuronyl-galactosyl-proteoglycan 4-
alpha-N-acetylglucosaminyltransferase
(2.4.1.223)
glucuronosyl-N-acetylglucosaminyl-
proteoglycan 4-alpha-N-
acetylglucosaminyltransferase (2.4.1.224)
N-acetylglucosaminyl-proteoglycan 4-
beta-glucuronosyltransferase (2.4.1.225)
N-acetylgalactosaminyl-proteoglycan 3-
beta-glucuronosyltransferase (2.4.1.226)
initiation-specific alpha-1,6-
mannosyltransferase (2.4.1.232)
N-acetyl-beta-glucosaminyl-glycoprotein
4-beta-N-acetylgalactosaminyltransferase
(2.4.1.244)
glutathione transferase (2.5.1.18)
squalene synthase (2.5.1.21)
ditrans,polycis-polyprenyl diphosphate
synthase (2.5.1.31)
4-hydroxybenzoate polyprenyltransferase
(2.5.1.39)
deoxyhypusine synthase (2.5.1.46)
all-trans-nonaprenyl diphosphate synthase
[geranylgeranyl-diphosphate specific]
(2.5.1.85)
4-hydroxybenzoate geranyltransferase
(2.5.1.93)
kynurenine-oxoglutarate transaminase
(2.6.1.7)
1-phosphatidylinositol 4-kinase (2.7.1.67)
diacylglycerol kinase (ATP dependent)
(2.7.1.107)
dolichol kinase (2.7.1.108)
inositol-trisphosphate 3-kinase (2.7.1.127)
phosphatidylinositol 3-kinase (2.7.1.137)
ADP-specific glucokinase (2.7.1.147)
1-phosphatidylinositol-5-phosphate 4-
kinase (2.7.1.149)
inositol-1,3,4-trisphosphate 5/6-kinase
(2.7.1.159)
diacylglycerol kinase (CTP dependent)
(2.7.1.174)
arginine kinase (2.7.3.3)
nucleoside-diphosphate kinase (2.7.4.6)
polyribonucleotide nucleotidyltransferase
(2.7.7.8)
ethanolamine-phosphate
cytidylyltransferase (2.7.7.14)
choline-phosphate cytidylyltransferase
(2.7.7.15)
polynucleotide adenylyltransferase
(2.7.7.19)
phosphatidate cytidylyltransferase
(2.7.7.41)
2'-5' oligoadenylate synthase (2.7.7.84)
ethanolaminephosphotransferase (2.7.8.1)
diacylglycerol cholinephosphotransferase
(2.7.8.2)
CDP-diacylglycerol-serine O-
phosphatidyltransferase (2.7.8.8)
CDP-diacylglycerol-inositol 3-
phosphatidyltransferase (2.7.8.11)
UDP-N-acetylglucosamine-dolichyl-
phosphate N-
acetylglucosaminephosphotransferase
(2.7.8.15)
UDP-N-acetylglucosamine-lysosomal-
enzyme N-
acetylglucosaminephosphotransferase
(2.7.8.17)
receptor protein-tyrosine kinase (2.7.10.1)
non-specific protein-tyrosine kinase
(2.7.10.2)
non-specific serine/threonine protein
kinase (2.7.11.1)
Goodpasture-antigen-binding protein
kinase (2.7.11.9)
cAMP-dependent protein kinase
(2.7.11.11)
cGMP-dependent protein kinase
(2.7.11.12)
protein kinase C (2.7.11.13)
Ca2+/calmodulin-dependent protein
kinase (2.7.11.17)
elongation factor 2 kinase (2.7.11.20)
histidine kinase (2.7.13.3)
thiosulfate sulfurtransferase (2.8.1.1)
steroid sulfotransferase (2.8.2.15)
Carboxylesterase (3.1.1.1)
Arylesterase (3.1.1.2)
triacylglycerol lipase (3.1.1.3)
Lysophospholipase (3.1.1.5)
Pectinesterase (3.1.1.11)
sterol esterase (3.1.1.13)
acylcarnitine hydrolase (3.1.1.28)
lipoprotein lipase (3.1.1.34)
retinoid isomerohydrolase (3.1.1.64)
palmitoyl-CoA hydrolase (3.1.2.2)
acyl-CoA hydrolase (3.1.2.20)
palmitoyl[protein] hydrolase (3.1.2.22)
phosphatidate phosphatase (3.1.3.4)
phosphatidylinositol-4-phosphate
phosphatase (3.1.3.B4)
3'-nucleotidase (3.1.3.6)
glucose-6-phosphatase (3.1.3.9)
phosphoprotein phosphatase (3.1.3.16)
sucrose-phosphate phosphatase (3.1.3.24)
4-phytase (3.1.3.26)
Nucleotidase (3.1.3.31)
phosphoinositide 5-phosphatase (3.1.3.36)
[hydroxymethylglutaryl-CoA reductase
(NADPH)]-phosphatase (3.1.3.47)
protein-tyrosine-phosphatase (3.1.3.48)
multiple inositol-polyphosphate
phosphatase (3.1.3.62)
phosphodiesterase I (3.1.4.1)
phospholipase C (3.1.4.3)
phospholipase D (3.1.4.4)
sphingomyelin phosphodiesterase
(3.1.4.12)
glycerophosphoinositol
glycerophosphodiesterase (3.1.4.44)
glycosylphosphatidylinositol
phospholipase D (3.1.4.50)
Arylsulfatase (3.1.6.1)
steryl-sulfatase (3.1.6.2)
deoxyribonuclease I (3.1.21.1)
ribonuclease T2 (3.1.27.1)
Aspergillus nuclease S1 (3.1.30.1)
oligo-1,6-glucosidase (3.2.1.10)
exo-alpha-sialidase (3.2.1.18)
alpha-glucosidase (3.2.1.20)

TABLE 12-continued

List of Golgi Enzymes (EC Number)

beta-glucosidase (3.2.1.21)
alpha-galactosidase (3.2.1.22)
alpha-mannosidase (3.2.1.24)
beta-fructofuranosidase (3.2.1.26)
beta-glucuronidase (3.2.1.31)
glucan 1 (3.2.1.84)
3alpha(S)-strictosidine beta-glucosidase (3.2.1.105)
mannosyl-oligosaccharide glucosidase (3.2.1.106)
Lactase (3.2.1.108)
mannosyl-oligosaccharide 1 (3.2.1.113)
glycoprotein endo-alpha-1 (3.2.1.130)
beta-D-glucopyranosyl abscisate beta-glucosidase (3.2.1.175)
rRNA N-glycosylase (3.2.2.22)
microsomal epoxide hydrolase (3.3.2.9)
soluble epoxide hydrolase (3.3.2.10)
leucyl aminopeptidase (3.4.11.1)
membrane alanyl aminopeptidase (3.4.11.2)
aminopeptidase B (3.4.11.6)
glutamyl aminopeptidase (3.4.11.7)
aminopeptidase I (3.4.11.22)
dipeptidyl-peptidase IV (3.4.14.5)
carboxypeptidase C (3.4.16.5)
carboxypeptidase A (3.4.17.1)
cathepsin X (3.4.18.1)
ubiquitinyl hydrolase 1 (3.4.19.12)
Duodenase (3.4.21.B3)
Neurosin (3.4.21.B10)
coagulation factor VIIa (3.4.21.21)
prolyl oligopeptidase (3.4.21.26)
proprotein convertase 7 (3.4.21.B27)
complement factor I (3.4.21.45)
Cerevisin (3.4.21.48)
Furin (3.4.21.75)
Signal peptidase I (3.4.21.89)
Proprotein convertase 1 (3.4.21.93)
rhomboid protease (3.4.21.105)
peptidase Do (3.4.21.107)
HtrA2 peptidase (3.4.21.108)
Matriptase (3.4.21.109)
site-1 protease (3.4.21.112)
bleomycin hydrolase (3.4.22.40)
calpain-2 (3.4.22.53)
caspase-2 (3.4.22.55)
caspase-4 (3.4.22.57)
EhCP4 proteinase (3.4.22.B68)
cathepsin D (3.4.23.5)
plasmepsin V (3.4.23.B19)
cathepsin E (3.4.23.34)
memapsin 1 (3.4.23.45)
memapsin 2 (3.4.23.46)
matrix metalloproteinase-20 (3.4.24.B6)
ADAM1 endopeptidase (3.4.24.B8)
procollagen N-endopeptidase (3.4.24.14)
PHEX peptidase (3.4.24.B15)
Insulysin (3.4.24.56)
ADAM10 endopeptidase (3.4.24.81)
Ste24 endopeptidase (3.4.24.84)
S2P endopeptidase (3.4.24.85)
ADAM 17 endopeptidase (3.4.24.86)
ADAMTS13 endopeptidase (3.4.24.87)
RCE1 (3.4.99.B1)
Asparaginase (3.5.1.1)
Biotinidase (3.5.1.12)
Ceramidase (3.5.1.23)
N4-(beta-N-acetylglucosaminyl)-L-asparaginase (3.5.1.26)
peptide-N4-(N-acetyl-beta-glucosaminyl)asparagine amidase (3.5.1.52)
N-acetylglucosaminylphosphatidylinositol deacetylase (3.5.1.89)
fatty acid amide hydrolase (3.5.1.99)
Allantoinase (3.5.2.5)
allantoate deiminase (3.5.3.9)
(S)-ureidoglycine aminohydrolase (3.5.3.26)
inorganic diphosphatase (3.6.1.1)
adenosinetriphosphatase (3.6.1.3)
Apyrase (3.6.1.5)
nucleoside diphosphate phosphatase (3.6.1.6)
nucleotide diphosphatase (3.6.1.9)
dolichyldiphosphatase (3.6.1.43)
phospholipid-translocating ATPase (3.6.3.1)
Cd2+-exporting ATPase (3.6.3.3)
Ca2+-transporting ATPase (3.6.3.8)
H+/K+-exchanging ATPase (3.6.3.10)
nitrate-transporting ATPase (3.6.3.26)
peptide-transporting ATPase (3.6.3.43)
cadmium-transporting ATPase (3.6.3.46)
fatty-acyl-CoA-transporting ATPase (3.6.3.47)
channel-conductance-controlling ATPase (3.6.3.49)
dynein ATPase (3.6.4.2)
microtubule-severing ATPase (3.6.4.3)
plus-end-directed kinesin ATPase (3.6.4.4)
vesicle-fusing ATPase (3.6.4.6)
non-chaperonin molecular chaperone ATPase (3.6.4.10)
heterotrimeric G-protein GTPase (3.6.5.1)
small monomeric GTPase (3.6.5.2)
signal-recognition-particle GTPase (3.6.5.4)
dynamin GTPase (3.6.5.5)
aminophospholipid translocase (3.6.99.B1)
phloretin hydrolase (3.7.1.4)
Histidine decarboxylase (4.1.1.22)
aromatic-L-amino-acid decarboxylase (4.1.1.28)
phosphatidylserine decarboxylase (4.1.1.65)
peptidyl-glutamate 4-carboxylase (4.1.1.90)
sphinganine-1-phosphate aldolase (4.1.2.27)
fumarate hydratase (4.2.1.2)
very-long-chain (3R)-3-hydroxyacyl-[acyl-carrier protein] dehydratase (4.2.1.134)
abieta-7 (4.2.3.18)
levopimaradiene synthase (4.2.3.32)
phenylalanine ammonia-lyase (4.3.1.24)
peptidylamidoglycolate lyase (4.3.2.5)
leukotriene-C4 synthase (4.4.1.20)
adenylate cyclase (4.6.1.1)
glycosylphosphatidylinositol diacylglycerol-lyase (4.6.1.14)
Peptidylprolyl isomerase (5.2.1.8)
Protein disulfide-isomerase (5.3.4.1)
Prostaglandin-D synthase (5.3.99.2)
prostaglandin-I synthase (5.3.99.4)
Thromboxane-A synthase (5.3.99.5)
Lysine-tRNA ligase (6.1.1.6)
long-chain-fatty-acid-CoA ligase (6.2.1.3)
Cholate-CoA ligase (6.2.1.7)
dicarboxylate-CoA ligase (6.2.1.23)
Phytanate-CoA ligase (6.2.1.24)
Ubiquitin-protein ligase (6.3.2.19)
glucuronate reductase (1.1.1.19)
hydroxymethylglutaryl-CoA reductase (NADPH) (1.1.1.34)
3-hydroxyacyl-CoA dehydrogenase (1.1.1.35)
acetoacetyl-CoA reductase (1.1.1.36)
11beta-hydroxysteroid dehydrogenase ((NAD+) (1.1.1.B40)
isocitrate dehydrogenase (NADP+) (1.1.1.42)
glucose 1-dehydrogenase [NAD(P)+] (1.1.1.47)

TABLE 12-continued

List of Golgi Enzymes (EC Number)

glucose-6-phosphate dehydrogenase (NADP+) (1.1.1.49)
3(or 17)beta-hydroxysteroid dehydrogenase (1.1.1.51)
3alpha(or 20beta)-hydroxysteroid dehydrogenase (1.1.1.53)
17beta-estradiol 17-dehydrogenase (1.1.1.62)
testosterone 17beta-dehydrogenase (NADP+) (1.1.1.64)
hydroxymethylglutaryl-CoA reductase (1.1.1.88)
3-oxoacyl-[acyl-carrier-protein] reductase (1.1.1.100)
3-dehydrosphinganine reductase (1.1.1.102)
all-trans-retinol dehydrogenase (NAD+) (1.1.1.105)
11beta-hydroxysteroid dehydrogenase (1.1.1.146)
21-hydroxysteroid dehydrogenase (NAD+) (1.1.1.150)
3beta-hydroxysteroid-4alpha-carboxylate 3-dehydrogenase (decarboxylating) (1.1.1.170)
carbonyl reductase (NADPH) (1.1.1.184)
prostaglandin-F synthase (1.1.1.188)
3beta-hydroxysteroid 3-dehydrogenase (1.1.1.270)
3beta-hydroxy-5alpha-steroid dehydrogenase (1.1.1.278)
NADP-retinol dehydrogenase (1.1.1.300)
11-cis-retinol dehydrogenase (1.1.1.315)
very-long-chain 3-oxoacyl-CoA reductase (1.1.1.330)
alcohol oxidase (1.1.3.13)
D-mannitol oxidase (1.1.3.40)
vitamin-K-epoxide reductase (warfarin-sensitive) (1.1.4.1)
vitamin-K-epoxide reductase (warfarin-insensitive) (1.1.4.2)
aminobutyraldehyde dehydrogenase (1.2.1.19)
alcohol-forming fatty acyl-CoA reductase (1.2.1.84)
dihydropyrimidine dehydrogenase (NADP+) (1.3.1.2)
acyl-CoA dehydrogenase (NADP+) (1.3.1.8)
7-dehydrocholesterol reductase (1.3.1.21)
3-oxo-5alpha-steroid 4-dehydrogenase (NADP+) (1.3.1.22)
phosphatidylcholine desaturase (1.3.1.35)
DELTA14-sterol reductase (1.3.1.70)
DELTA24(241)-sterol reductase (1.3.1.71)
DELTA24-sterol reductase (1.3.1.72)
tRNA-dihydrouridine20 synthase [NAD(P)+] (1.3.1.91)
very-long-chain enoyl-CoA reductase (1.3.1.93)
secologanin synthase (1.3.3.9)
all-trans-retinol 13 (1.3.99.23)
glutamate dehydrogenase [NAD(P)+] (1.4.1.3)
protein-lysine 6-oxidase (1.4.3.13)
cytochrome-b5 reductase (1.6.2.2)
NADPH-hemoprotein reductase (1.6.2.4)
NAD(P)H oxidase (H2O2-forming) (1.6.3.1)
glutathione reductase (NADPH) (1.6.4.2)
NAD(P)H dehydrogenase (quinone) (1.6.5.2)
monodehydroascorbate reductase (NADH) (1.6.5.4)
azobenzene reductase (1.7.1.6)
protein-disulfide reductase (1.8.1.8)
thiol oxidase (1.8.3.2)
protein-disulfide reductase (glutathione) (1.8.4.2)
peptide-methionine (R)—S-oxide reductase (1.8.4.12)
dimethylsulfoxide reductase (1.8.5.3)
iodide peroxidase (1.11.1.8)
glutathione peroxidase (1.11.1.9)
L-ascorbate peroxidase (1.11.1.11)
Peroxiredoxin (1.11.1.15)
prostamide/prostaglandin F2alpha synthase (1.11.1.20)
4-hydroxyphenylpyruvate dioxygenase (1.13.11.27)
Renilla-luciferin 2-monooxygenase (1.13.12.5)
procollagen-proline dioxygenase (1.14.11.2)
procollagen-lysine 5-dioxygenase (1.14.11.4)
procollagen-proline 3-dioxygenase (1.14.11.7)
peptide-aspartate beta-dioxygenase (1.14.11.16)
proline 3-hydroxylase (1.14.11.28)
flavin-containing monooxygenase (1.14.13.8)
trans-cinnamate 4-monooxygenase (1.14.13.11)
phosphatidylcholine 12-monooxygenase (1.14.13.26)
albendazole monooxygenase (1.14.13.32)
nitric-oxide synthase (NADPH dependent) (1.14.13.39)
(S)-limonene 3-monooxygenase (1.14.13.47)
(S)-limonene 6-monooxygenase (1.14.13.48)
isoflavone 3'-hydroxylase (1.14.13.52)
sterol 14alpha-demethylase (1.14.13.70)
N-methylcoclaurine 3'-monooxygenase (1.14.13.71)
methylsterol monooxygenase (1.14.13.72)
tabersonine 16-hydroxylase (1.14.13.73)
taxane 10beta-hydroxylase (1.14.13.76)

The examples below are given so as to illustrate the practice of this invention. They are not intended to limit or define the entire scope of this invention.

EXAMPLE 1

Preparation of a 7-Nitrobenzofurazan-Based Endoplasmic Reticulum-Targeted Dye 4-maleimido-1-butanammonium trifluoroacetate (M1959)

To a 250 mL round-bottom flask was added 4-amino-1-butanol (1.56 mL, 16.9 mmol) and water (35.0 mL). The solution was cooled to 0° C., and sodium bicarbonate (2.83 g, 33.7 mmol) was added. After 5 min, t-Boc anhydride (5.52 g, 25.3 mmol) in THF (5.0 mL) was added. After 17.5 h, the reaction solution was extracted with dichloromethane (3×50 mL). The organic layer was washed with water (2×50 mL), dried over MgSO$_4$ and concentrated in vacuo. The resulting crude t-Boc carbamate (3.99 g) was added to a 100 mL round-bottom flask containing triphenylphosphine (4.88 g, 18.6 mmol) and maleimide (1.81 g, 18.6 mmol) in THF (50 mL). After 15 min, diisopropyl azodicarboxylate (4.00 mL, 20.3 mmol) was added. This reaction solution was allowed to stir for 16 h, the solution was concentrated in vacuo and the product purified via flash chromatography over SiO$_2$, eluting with 40% to 60% ethyl acetate/hexanes.

The resulting 4-maleimidobutanamine t-Boc carbamate (6.87 g, containing some remaining impurities observed via TLC) was added to a 250 mL round-bottom flask and dissolved in dichloromethane (40 mL). Water (5.0 mL) and trifluoroacetic acid (25.0 mL) were added. After 1 h, the solution was diluted with dichloromethane (150 mL) and extracted with water (3×100 mL). The aqueous layer was washed with dichloromethane (2×100 mL) and concentrated and dried in vacuo. The resulting oil was recrystallized from ethyl acetate (75 mL) to give M1959 (2.23 g, 7.90 mmol, 47% three-step yield) as a pale yellow solid. TLC (10% methanol/dichloromethane) Rf=0.15.

4-(4-maleimidobutanamino)-7-nitrobenzofurazan (M2419)

To a 50 mL round-bottom flask was added M1959 (282.2 mg, 1.00 mmol), water (2.0 mL) and tetrahydrofuran (8.0 mL). To the stirred solution was added 4-chloro-7-nitrobenzofurazan (299 mg, 1.50 mmol). After 10 min, triethylamine (0.418 mL, 3.00 mmol) was added dropwise. The solution was stirred at room temperature in the absence of light. After 17 h, the reaction solution was diluted with ethyl acetate (200 mL) and water (200 mL). The organic layer was separated and dried over $MgSO_4$ and concentrated in vacuo. The resulting residue was purified by flash chromatography over $SiO_2$, eluting with 20% to 50% ethyl acetate/hexanes, to give M2419 (30.5 mg, 92.1 μmol, 9%) as a brown solid. TLC (50% ethyl acetate/hexanes) Rf=0.23; $^1$H NMR (DMSO-$d_6$, 300 MHz): δ=9.49 (br s, 1H), 8.48 (d, J=8.8 Hz, 1H), 6.99 (s, 2H), 6.40 (d, J=8.8 Hz, 1H), 3.45-3.43 (m, 4H), 2.49-2.48 (m, 4H).

4-(4-maleimidobutanamino)-7-nitrobenzofurazan, Conjugated to ER-Targeting Peptide To a 1.5 mL Eppendorf tube was added a solution of M2419 (100 μL, 2.0 mM in acetone, 0.2 μmol), a solution of NHAc—C—F—F—K-D-E-L-COOH (100 μL, 1.0 mM in 1:1 ethanol/water, 0.1 μmol) and a solution of triethylamine (100 μL, 0.10 mM in water, 0.010 μmol). After gently agitating the vial for 18 h, the solution was diluted in water (500 μL) and extracted with chloroform (3×500 μL). The aqueous layer was lyophilized to give M2422, homogeneous by TLC (10% acetic acid/methanol) Rf=0.85.

EXAMPLE 2

Preparation of a 7-Nitrobenzofurazan-Based Golgi Apparatus-Targeted Probe 4-(4-maleimidobutanamino)-7-nitrobenzofurazan, Conjugated to Golgi-Targeting Peptide (M2423)

To a 1.5 mL Eppendorf tube was added a solution of M2419 (100 μL, 2.0 mM in acetone, 0.2 μmol), a solution of $H_2N$-G-A-S-D-Y-Q-R-L-C—COOH (SEQ ID NO:7) (100 μL, 1.0 mM in water, 0.1 μmol) and a solution of triethylamine (100 μL, 0.10 mM in water, 0.010 μmol). After gently agitating the vial by inversion for 18 h, the solution was diluted into water (500 μL) and extracted with chloroform (3×500 μL). The aqueous layer was lyophilized to give M2423, homogeneous by TLC (10% acetic acid/methanol) Rf=0.11.

EXAMPLE 3

Preparation of a Resorufin-Based α-Mannosidase Substrate Targeted to the Endoplasmic Reticulum Exhibiting Red Fluorescence After Enzyme Activity N-Hydroxysuccinimide Trifluoroacetate (M1027)

To a flame-dried 25 mL round-bottom flask was added N-hydroxysuccinimide (1.15 g, 10.0 mmol) and trifluoroacetic anhydride (3.80 mL, 27.5 mmol). After 2 h, the solution was concentrated in vacuo, co-evaporated with toluene (2×25 mL) and dried in vacuo to give M1027 (2.03 g, 9.62 mmol, 96%) as a white solid.

2-chloro-6-carboxyresorufin (M2458)

To a flame-dried 250-mL round-bottom flask was added 4-nitroso-6-chlororesorcinol (6.94 g, 40.0 mmol) and 2,6-dihydroxybenzoic acid (6.16 g, 40.0 mmol), and the solids dissolved slowly into conc. sulfuric acid (40.0 mL). The stirred solution was heated to 107° C. for 35 min., and the resulting red/brown solution was allowed to cool to room temperature, poured into ice-cold water (300 mL). After stirring for 15 min, the red precipitate was collected by suction filtration, washed with $H_2O$ until the filtrate pH was neutral and dried in vacuo to give M2458 9.48 g, 32.5 mmol, 81%) as a dark red/brown solid. TLC (9:1:1 dichloromethane/methanol/acetic acid) Rf=0.33.

2-chloro-6-carboxyresorufin, NHS Ester (M2461)

To a flame-dried 100 mL round-bottom flask was added M2458 (583.2 mg, 2.00 mmol), N,N-dimethylformamide (20.0 mL) and crushed 3 Å molecular sieves (800 mg). To a separate 20 mL vial was added M1027 (506.5 mg, 2.40 mmol) and N,N-dimethylformamide (5.0 mL), followed by pyridine (0.195 mL, 2.40 mmol). The M1027 solution was pipette slowly into the M2458 solution with stirring. After 17 h, diisopropylethylamine (374.1 μL, 2.09 mmol) was added to aid solubilization. After 1 h, additional M1027 (507.2 mg, 2.40 mmol) were added. After 24 h, additional M1027 (505.3 mg, 2.40 mmol) were added. After 4 h, additional M1027 (251.7 mg, 1.19 mmol) were added. After 2 h, the reaction solution was diluted with ethyl acetate (300 mL) and washed with saturated aqueous ammonium chloride solution (3×100 mL). The organic layer was dried over anhydrous $MgSO_4$ and concentrated in vacuo to a minimal volume, and then precipitated by addition of diethyl ether (500 mL). The precipitate was collected and dried in vacuo to give M2461 (339.1 mg, 0.872 mmol, 44%). TLC (10% methanol/dichloromethane) Rf=0.10.

2-chloro-6-(4-maleimidobutanecarboxamido)resorufin (M2485)

To a flame-dried 25-mL round-bottom flask under anhydrous $N_{2(g)}$ was added M2461 (582.8 mg, 1.50 mmol) and N,N-dimethylformamide (6.5 mL). Diisopropylethylamine (0.281 mL, 1.65 mmol) was next added to the stirred solution, followed by 4-maleimido-1-butanamine (465.7 mg, 1.65 mmol). After stirring under anhydrous condition at room temperature for 17 h, the stirred solution was diluted with ethyl acetate (100 mL) and $H_2O$ (100 mL), resulting in a red precipitate. The precipitate was collected via vacuum filtration, washed with $H_2O$ (50 mL) followed by ethyl acetate (50 mL), then dried in vacuo to give M2485 (220.9 mg, 500.0 mmol, 33% yield) as a bright red solid. TLC (10% methanol/dichloromethane) Rf=0.52; $^1$H NMR (DMSO-d$_6$, 300 MHz): δ=9.18 (br s, 1H), 7.59 (s, 1H), 7.34 (d, J=9.7 Hz, 1H), 7.04 (s, 2H), 6.47 (d, J=9.4 Hz, 1H), 6.06 (s, 1H), 3.46 (t, J=6.6 Hz, 2H), 3.23 (q, J=6.2 Hz, 2H), 1.63-1.57 (m, 2H), 1.47-1.45 (m, 2H).

2-chloro-6-(4-maleimidobutanecarboxamido)resorufin α-mannoside tetraacetate (M2492)

To a dry 20 mL vial was prepared a solution of M2485 (35.9 mg, 81.3 μmol) in acetonitrile (1.6 mL). Sym-collidine (10.7 μL, 81.3 μmol) was added, followed by acetobromomannose (43.6 mg, 106 μmol) in dichloromethane (0.41 mL). Silver carbonate (14.0 mg, 50.8 μmol) was added, and the solution was stirred at room temperature under anyhydrous condition and in the absence of light. After 18 h, diisopropylethylamine (13.8 μL, 81.3 μmol) was added to enhance the solubility of the dye as well as acetobromomannose (60 mg in 500 μL diethyl ether) and silver carbonate (14.6 mg, 52.9 μmol) were added. After an additional 18 h of stirring as above, powdered 3 Å molecular sieves (199.4 mg) were added, followed by acetobromomannose (115.1 mg) in acetonitrile (1.0 mL), sym-collidine (10.7 μL) and silver carbonate (45.0 mg). After an additional 21 h of stirring, the reaction solution was filtered through Celite™ 545 to remove precipitated silver salts. The solution was diluted with ethyl acetate (30 mL) and washed with saturated aqueous ammonium chloride solution (50 mL). The dried organic layer (MgSO$_4$) was concentrated in vacuo. The product was purified via preperative TLC, eluting with 20% acetone/dichloromethane, to give M2492 (10.1 mg, 13.1 μmol, 16%) as an orange solid. TLC (20% acetone/dichloromethane) Rf=0.46.

2-chloro-6-(4-maleimidobutanecarboxamido)resorufin α-mannoside tetraacetate, Conjugated to ER-Targeting Peptide (M2496)

To a 4 mL vial was added a solution of M2492 (1.0 mL, 2.0 mM in acetone, 2.0 μmol), a solution of AcHN—C—F—F—K-D-E-L-COOH (SEQ ID NO:6) (1.0 mL, 1.0 mM in 1:1 water/ethanol, 1.0 μmol), and a solution of triethylamine (1.0 mL, 0.10 mM in water, 0.10 μmol). After gently agitating for 18 hours at ambient temperature, the solution was diluted with water (3.0 mL) and the excess dye was extracted with dichloromethane (3×1.0 mL). The resulting aqueous layer was concentrated via lyophilization to give M2496 (1.0 mg, 0.55 μmol, 55%) as an orange solid. TLCs (7:3:1 dichloromethane/methanol/acetic acid) Rf=0.20.

EXAMPLE 4

Preparation of a Resorufin-Based α-Mannosidase Substrate Targeted to the Golgi Apparatus Exhibiting Red Fluorescence After Enzyme Activity 2-chloro-6-(4-maleimidobutanecarboxamido)resorufin α-mannoside tetraacetate, Conjugated to Golgi Apparatus-Targeting Peptide (M2497)

To a 4 mL vial was added a solution of M2492 (1.0 mL, 2.0 mM in acetone, 2.0 μmol), a solution of H$_2$N-G-A-S-D-Y-Q-R-L-C—COOH (SEQ ID NO:7) (1.0 mL, 1.0 mM in water, 1.0 μmol), and a solution of triethylamine (1.0 mL, 0.10 mM in water, 0.10 μmol). After gently agitating this mixture for 18 h, the solution was diluted with water (3.0 mL) and the excess dye was extracted away with dichloromethane (3×1.0 mL). The resulting aqueous layer was concentrated via lyophilization to give M2497 (0.8 mg, 0.36 μmol, 36%) as an orange solid homogeneous by TLC (7:3:1 dichloromethane/methanol/acetic acid) with Rf=0.01.

EXAMPLE 5

Preparation of a Resorufin-Based α-Mannosidase Substrate Containing a Non-Targeting Peptide Sequence Exhibiting Red Fluorescence After Enzyme Activity 2-chloro-6-(4-maleimidobutanecarboxamido)resorufin α-mannoside tetraacetate, Conjugated to Nonsense Peptide (M2498)

To a dry 4 mL vial was added a solution of M2492 (1.0 mL, 2.0 mM in acetone, 2.0 μmol), a solution of NHAc-C-G-G-G-G-G-(D-A)-COOH (SEQ ID NO:24) (1.0 mL, 1.0 mM in water, 1.0 μmol), and a solution of triethylamine (1.0 mL, 0.10 mM in water, 0.10 μmol). After mixing by inversion for 18 h, the solution was diluted with water (3.0 mL) and the excess dye was extracted with dichloromethane (3×1.0 mL). The remaining aqueous layer was concentrated via lyophilization to give M2498 (1.2 mg, 0.93 μmol, 93%) as an orange solid homogeneous by SiO$_2$TLC (7:3:1 dichloromethane/methanol/acetic acid) Rf=0.15.

EXAMPLE 6

Preparation of a Resorufin-Based β-Glucosidase Substrate Targeted to the Endoplasmic Reticulum Exhibiting Red Fluorescence After Enzyme Activity 2-chloro-6-(4-maleimidobutanecarboxamido)resorufin β-glucoside tetraacetate (M2548)

To a flame-dried 10 mL round-bottom flask under dry N$_2$ (g) was added M2485 (45.0 mg, 0.102 mmol), acetonitrile (2.0 mL) and dichloromethane (0.50 mL), followed by diisopropylethylamine (17.0 μL, 0.100 mmol). Acetobromoglucose (51.5 mg, 0.125 mmol), sym-collidine (13.2 μL) and silver carbonate (17.4 mg, 0.063 mmol) were then added, and the solution was stirred vigorously under anhydrous condition, in the absence of light overnight. After 24 h, additional acetobromoglucose (51.2 mg, 0.125 mmol), silver carbonate (17.4 mg, 0.063 mmol) and sym-collidine (13.2 μL, 0.100 mmol) were added. After 3 days stirring as above, the solution was filtered through Celite™ 545, washing the precipitated salts with ethyl acetate. The filtrate was concentrated in vacuo and diluted in ethyl acetate (30 mL). The organic solution was washed with saturated aqueous ammonium chloride (30 mL), dried over anhydrous MgSO$_4$ and concentrated in vacuo. The product was purified by preparative TLC, eluting with 20% acetone/dichloromethane, to give M2548 (17.4 mg, 22.5 μmol, 22%) as an orange solid. TLC (10% methanol/dichloromethane) Rf=0.36.

2-chloro-6-(4-maleimidobutanecarboxamido)resorufin β-glucoside tetraacetate, Conjugated to ER-Targeting Peptide (M2550)

To a 4 mL vial was added a solution of M2548 (1.0 mL, 2.0 mM in acetone, 2.0 μmol), a solution of AcHN—C—F—F—K-D-E-L-COOH (SEQ ID NO:6) (1.0 mL, 1.0 mM in 1:1 water/ethanol, 1.0 μmol), and a solution of triethylamine (1.0 mL, 0.10 mM in water, 0.10 µmol). After gently agitating for 17 h, the solution was diluted with water (3.0 mL) and the excess dye was extracted with dichloromethane (3×3.0 mL). The aqueous layer was concentrated via lyophilization to give M2550 (0.7 mg, 0.40 µmol, 40%) as an orange solid. TLC (10% methanol/dichloromethane) Rf=0.00.

EXAMPLE 7

Preparation of a Resorufin-Based β-Glucosidase Substrate Targeted to the Golgi Apparatus Exhibiting Red Fluorescence After Enzyme Activity 2-chloro-6-(4-maleimidobutanecarboxamido)resorufin β-glucoside tetraacetate, Conjugated to Golgi Apparatus-Targeting Peptide (M2551)

To a 4 mL vial was added a solution of M2548 (1.0 mL, 2.0 mM in acetone, 2.0 µmol), a solution of H$_2$N-G-A-S-D-Y-Q-R-L-C—COOH (SEQ ID NO:7) (1.0 mL, 1.0 mM in water, 1.0 µmol), and a solution of triethylamine (1.0 mL, 0.10 mM in water, 0.10 µmol). After mixing by inversion for 17 h, the solution was diluted with water (3.0 mL) and the excess dye was extracted with dichloromethane (3×3.0 mL). The aqueous layer was concentrated via lyophilization to give M2551 (1.5 mg, 0.83 µmol, 83%) as an orange solid. TLC (10% methanol/dichloromethane) Rf=0.00.

EXAMPLE 8

Preparation of a Resorufin-Based β-Glucosidase Substrate Containing a Non-Targeting (Nonsense) Peptide Sequence Exhibiting Nonspecific Red Fluorescence Staining After Enzyme Activity 2-chloro-6-(4-maleimidobutanecarboxamido)resorufin β-glucoside tetraacetate, Conjugated to Nonsense Peptide (M2552)

To a 4 mL vial was added a solution of M2548 (1.0 mL, 2.0 mM in acetone, 2.0 µmol), a solution of AcHN—C-G-G-G-G-G-(D-A)-COOH (SEQ ID NO:24) (1.0 mL, 1.0 mM in water, 1.0 µmol), and a solution of triethylamine (1.0 mL, 0.10 mM in water, 0.10 µmol). After gently agitating for 17 h, the solution was diluted with water (3.0 mL) and the excess dye was extracted with dichloromethane (3×3.0 mL). The aqueous layer was concentrated via lyophilization to give M2552 (0.9 mg, 0.73 µmol, 73%) as an orange solid. TLC (10% methanol/dichloromethane) Rf=0.00.

EXAMPLE 9

Preparation of a Rhodamine 110-Based Aspartase Substrate Targeted to the Endoplasmic Reticulum, Producing Green Fluorescence Upon Enzyme Activity Rhodamine 110, Mono-3-Maleimidopropionamide (M2424)

To a flame-dried 25 mL round-bottom flask under anhydrous conditions (dry N$_{2(g)}$) was added 4-maleimidobutyric acid (275.7 mg, 1.51 mmol) and N,N-dimethylformamide (2.0 mL), followed by EDC.HCl (288.8 mg, 1.51 mmol) and diisopropylethylamine (0.510 mL, 3.00 mmol). After 45 min, a solution of rhodamine 110 hydrochloride (366.5 mg, 1.00 mmol) and diisopropylethylamine (0.170 mL, 1.00 mmol) in N,N-dimethylformamide (2.0 mL) was added to the 4-maleimidobutyric acid solution. After 19.5 h, further solutions of 4-maleimidobutyric acid (280.6 mg, 1.53 mmol), EDC.HCl (290.8 mg, 1.52 mmol) and diisopropylethylamine (0.510 mL, 3.00 mmol) in N,N-dimethylformamide (1.0 mL) was added to the stirred reaction solution. And a solution of 4-maleimidobutyric acid (97.6 mg, 0.533 mmol), EDC.HCl (98.4 mg, 0.513 mmol) and diisopropylethylamine (0.170 mL, 1.00 mmol) in N,N-dimethylformamide (1.0 mL) was added after 1 h. This solution was allowed to stir at room temperature for 16 h, diluted with ethyl acetate (150 mL) and washed with water (3×100 mL). The solution was dried over anhydrous MgSO$_4$ and concentrated in vacuo. The resulting residue was purified via flash chromatography on silica gel G (70-300 mesh), eluting using a gradient of 0% to 30% acetone/dichloromethane to give M2424 (239.2 mg, 0.483 mmol, 48%) as a bright orange solid. TLC (50% acetone/dichloromethane) Rf=0.40.

Rhodamine 110, Mono-3-Maleimidopropionamide, Mono-Cbz-Asp(t-Bu) (M2435)

To a 20 mL vial was added Cbz-Asp(t-Bu)—OH (199.7 mg, 618 µmol), EDC.HCl (118.4 mg, 618 µmol), N,N-dimethylformamide (1.0 mL) and pyridine (0.50 mL). After 40 min, M2424 (30.6 mg, 61.8 µmol) in N,N-dimethylformamide (1.0 mL) was added. After 17 h, the stirred solution was diluted with ethyl acetate (25 mL) and washed with water (25 mL), 1.0 N aq. HCl (2×10 mL), saturated. aq. NaHCO$_3$ (3×10 mL) and saturated aq. NaCl (30 mL). The organic layer was dried over anhydrous MgSO$_4$, filtered and concentrated in vacuo. The resulting residue was purified by preparative TLC, eluting with 10% methanol/dichloromethane, to give M2435 (28.7 mg, 35.8 µmol, 58%) as a white solid. TLC (10% methanol/dichloromethane) Rf=0.58.

Rhodamine 110, Mono-3-Maleimidopropionamide, Mono-Cbz-Asp(t-Bu), Conjugated to ER-Targeting Peptide (M2444)

To a 1.5 mL Eppendorf tube was added a solution of M2435 (300 µL, 2.0 mM in acetone, 0.60 µmol), a solution of AcHN—C—F—F—K-D-E-L-COOH (SEQ ID NO:6) (300 µL, 1.0 mM in 1:1 ethanol/water, 0.30 µmol), and a solution of triethylamine (300 µL, 0.10 mM in water, 0.010 µmol), and acetone (300 µL) to assist in dissolution of M2435. After mixing gently for 18 h, the solution was diluted with water (1.0 mL) and extracted with ethyl acetate (3×1.0 mL) to remove excess reagents. The aqueous solution was lyophilized to give M2444 (0.3 mg, 0.17 µmol, 57%) as a white solid, homogeneous by TLC (7:3:1 dichloromethane/methanol/acetic acid) Rf=0.57.

EXAMPLE 10

Preparation of a Rhodamine 110-Based Aspartase Substrate Targeted to the Golgi Apparatus, Producing Green Fluorescence Upon Enzyme Activity Rhodamine 110, Mono-3-Maleimidopropionamide, Mono-Cbz-Asp(t-Bu), Conjugated to Golgi Apparatus-Targeting Peptide (M2445)

To a 1.5 mL Eppendorf tube was added a solution of M2435 (300 µL, 2.0 mM in acetone, 0.60 µmol), a solution of H₂N-G-A-S-D-Y-Q-R-L-C—COOH (SEQ ID NO:7) (300 µL, 1.0 mM in water, 0.30 µmol), and a solution of triethylamine (300 µL, 0.10 mM in water, 0.010 µmol), followed by additional acetone (300 µL) to assist in dissolution of M2435. After gently agitating for 18 h, the solution was diluted with water (1.0 mL) and extracted with ethyl acetate (3×1.0 mL). The aqueous solution was lyophilized to give M2445 (0.5 mg, 0.28 µmol, 92%) as a white solid. TLC (7:3:1 dichloromethane/methanol/acetic acid) Rf=0.01.

EXAMPLE 11

Preparation of a Rhodamine 110-Based Aspartase Substrate Containing a Non-Targeting (Nonsense) Peptide Sequence, Producing Nonspecific Green Fluorescence Staining Upon Enzyme Activity Rhodamine 110, Mono-3-Maleimidopropionamide, Mono-Cbz-Asp(t-Bu), Conjugated to Nonsense Peptide (M2453)

To a 1.5 mL Eppendorf tube was added a solution of M2435 (300 µL, 2.0 mM in acetone, 0.60 µmol), a solution of AcHN-C-G-G-G-G-G-(D-A)-COOH (SEQ ID NO:24) (300 µL, 1.0 mM in water, 0.30 µmol), and a solution of triethylamine (300 µL, 0.10 mM in water, 0.010 µmol) and acetone (300 µL) to assist in dissolution of M2435. After gently agitating for 18 h, the solution was diluted with water (1.0 mL) and extracted with ethyl acetate (3×1.0 mL). The aqueous solution was lyophilized to give M2453 (0.4 mg, 0.30 µmol, 100%) as a white solid, homogenous by SiO₂ TLC (7:3:1 dichloromethane/methanol/acetic acid) Rf=0.24.

EXAMPLE 12

Preparation of a Rhodamine 110-Based Furin Substrate Targeted to the Endoplasmic Reticulum, Producing Green Fluorescence Upon Enzyme Activity Rhodamine 110, Mono-3-Maleimidopropionamide, Mono-Boc-Arg(Pmc) (M2571)

To a flame-dried 10 mL round-bottom flask under dry N₂(g) was added Boc-Arg(Pmc)-OH (541.9 mg, 1.00 mmol), N,N-dimethylformamide (2.0 mL) and pyridine (2.0 mL), followed by EDC.HCl (192.5 mg, 1.00 mmol). After 45 min, M2424 (99.1 mg, 0.200 mmol) in N,N-dimethylformamide (1.0 mL) was added. After stirring at ambient temperature under anhydrous conditions for 17 h, the reaction solution was diluted in ethyl acetate (50 mL) and washed with water (3.×.50 mL) and saturated aq. NaCl (50 mL). The organic layer was dried over anhydrous Na₂SO₄, filtered and concentrated in vacuo. The resulting residue was purified twice by preparative TLC, eluting each time with 30% methanol/dichloromethane, to give M2571 (47.7 mg, 96.3 µmol, 48%) as a white solid. TLC (10% methanol/dichloromethane) Rf=0.43.

Rhodamine 110, Mono-3-Maleimidopropionamide, Mono-H-Arg(Pmc) (M2517)

To a 2 mL vial was added M2571 (25.5 mg, 25.0 µmol), acetonitrile (200 µL) and dichloromethane (100 µL). This solution was cooled to 0° C. (ice-bath), and sodium iodide (4.4 mg, 29.4 µmol) was added. After 10 min, trimethylsilyl chloride (3.44 µL, 27.1 µmol) was added. After 40 min, additional sodium iodide (4.2 mg, 28.0 µmol) and trimethylsilyl chloride (3.44 µL, 27.1 µmol) was added. After 1.5 h, the solution was warmed to room temperature and additional acetonitrile (200 µL) was added. After observing starting material precipitating out of solution, additional dichloromethane was added dropwise until starting material was fully dissolved. Additional trimethylsilyl chloride (3.44 µL, 27.1 µmol) was added. After 35 min., additional sodium iodide (4.5 mg, 30.0 µmol) and trimethylsilyl chloride (6.88 µL, 54.2 µmol) was added. After 45 min, a final aliquot of trimethylsilyl chloride (6.88 µL, 54.2 µmol) was added. After 45 min, the reaction was quenched with methanol (100 µL). The solution was diluted with ethyl acetate (7 mL) and washed with 1.0 N aq. HCl (3×5 mL), saturated. aq. NaHCO₃ (3×5.0 mL) and saturated. aq. NaCl (5.0 mL). The dried organic layer (MgSO₄) was concentrated in vacuo to give M2517 (12.4 mg, 13.0 µmol, 52%) as a pale yellow solid. TLC (10% methanol/dichloromethane) Rf=0.21.

Rhodamine 110, Mono-3-Maleimidopropionamide, Mono-AcHN-Arg(Pmc)-Arg(Pmc)-Val-Arg(Pmc) (M2522)

To a flame-dried 10 mL round-bottom flask is added M2517 (10.1 mg, 11.0 µmol) and N,N-dimethylformamide (100 µL). To a separate 1.5 mL Eppendorf tube is added AcHN-Arg(Pmc)-Val-Arg(Pmc)-OH (12.1 mg, 12.1 µmol) and N,N-dimethylformamide (120 µL). EDC.HCl (2.3 mg, 12.1 µmol) and diisopropylethylamine (5.6 µL, 33.0 µmol) is then added to the peptide solution. After allowing it to stand 40 min., the peptide solution is added to the M2522 solution. This mixture is allowed to mix for 18 h, the solution is diluted with ethyl acetate (1.0 mL) and washed with water (1.0 mL), 1.0 N aq. HCl (3×500 µL), saturated. aq. NaHCO₃ (3×500 µL) and saturated. aq. NaCl (1.0 mL). The organic layer is dried over anhydrous MgSO₄ and concentrated in vacuo. The residue is purified by preparative TLC, eluting with 10% methanol/dichloromethane, to give M2522 as a white solid.

Rhodamine 110, Mono-3-Maleimidopropionamide, Mono-AcHN-Arg(Pmc)-Arg(Pmc)-Val-Arg(Pmc), Conjugated to ER-Targeting Peptide To a 1.5 mL Eppendorf tube is added M2522 (500 µL, 2.0 mM in acetone, 1.0 µmol), a solution of AcHN—C—F—F—K-D-E-L-COOH (SEQ ID NO:6) (500 µL, 1.0 mM in 1:1 ethanol/water, 0.50 µmol) and triethylamine (500 µL, 0.10 mM in water, 0.050 µmol). After gently agitating for 18 h, the solution is diluted in water (3.0 mL) and extracted with dichloromethane (3×1.0 mL) to remove the excess dye and starting materials. The resulting aqueous layer is then lyophilized to give M2556 as a white solid.

Rhodamine 110, Mono-3-Maleimidopropionamide, Mono-AcHN-Arg-Arg-Val-Arg, Conjugated to ER-Targeting Peptide To a 1.5 mL Eppendorf tube is added M2556 (0.50 µmol) and N,N-dimethylformamide (49.0 µL) and anhydrous hydrazine (1.0 µL). After 1 h, the product is precipitated with diethyl ether (500 µL). The solvent and excess hydrazine is removed via centrifugation and decanting, and the remaining residue is dried in vacuo to give the title targeted furin substrate. TLC (10% methanol/dichloromethane) Rf=0.00.

EXAMPLE 13

Preparation of a Rhodamine 110-Based Furin Substrate Targeted to the Golgi Apparatus, Producing Green Fluorescence Upon Enzyme Activity Rhodamine 110, Mono-3-Maleimidopropionamide, Mono-AcHN-Arg(Pmc)-Arg(Pmc)-Val-Arg(Pmc), Conjugated to Golgi-Targeting Peptide (M2579)

To a 1.5 mL Eppendorf tube is added M2522 (500 µL, 2.0 mM in acetone, 1.0 µmol), a solution of $H_2N$-G-A-S-D-Y-Q-R-L-C—COOH (SEQ ID NO:7) (500 µL, 1.0 mM in water, 0.50 µmol) and triethylamine (500 µL, 0.10 mM in water, 0.050 µmol). After gently agitating for 18 h, the solution is diluted in water (3.0 mL) and extracted with dichloromethane (3×1.0 mL) to remove excess starting materials. The resulting aqueous layer is lyophilized to give M2579 as a white solid. TLC (10% methanol/dichloromethane) Rf=0.00.

Rhodamine 110, Mono-3-Maleimidopropionamide, Mono-AcHN-Arg-Arg-Val-Arg, Conjugated to ER-Targeting Peptide, Golgi-Targeting Peptide, and Nonsense Peptide To a 1.5 mL Eppendorf tube is added M2579 (0.50 µmol) and N,N-dimethylformamide (49.0 µL) and anhydrous hydrazine (1.0 µL). After 1 h, the product is precipitated with diethyl ether (500 µL). The solvent and excess hydrazine is removed via centrifugation and decanting, and the remaining residue is dried in vacuo to give the desired targeted furin substrate.

EXAMPLE 14

Preparation of a Rhodamine 110-Based Furin Containing a Non-targeting Peptide (Nonsense) Sequence, Producing Nonspecific Green Fluorescence Staining Upon Enzyme Activity Rhodamine 110, Mono-3-Maleimidopropionamide, Mono-AcHN-Arg(Pmc)-Arg(Pmc)-Val-Arg(Pmc), Conjugated to Nonsense Peptide (M2580)

To a 1.5 mL Eppendorf tube is added M2522 (500 µL, 2.0 mM in acetone, 1.0 µmol), a solution of AcHN—C-G-G-G-G-G-(D-A)-COOH (SEQ ID NO:24) (500 µL, 1.0 mM in water, 0.50 µmol) and triethylamine (500 µL, 0.10 mM in water, 0.050 µmol). After gently agitating for 18 h, the solution is diluted in water (3.0 mL) and extracted with dichloromethane (3×1.0 mL) to remove excess starting materials. The aqueous layer is lyophilized to give M2580 as a white solid. TLC (10% methanol/dichloromethane) Rf=0.00.

Rhodamine 110, Mono-3-Maleimidopropionamide, Mono-AcHN-Arg-Arg-Val-Arg, Conjugated to ER-Targeting Peptide, Golgi-Targeting Peptide, and Nonsense Peptide To a 1.5 mL Eppendorf tube is added M2580 (0.50 µmol) and N,N-dimethylformamide (49.0 µL) and anhydrous hydrazine (1.0 µL). After 1 h, the product is precipitated with diethyl ether (500 µL). The solvent and excess hydrazine is removed via centrifugation and decanting, and the remaining residue is dried in vacuo to give the desired title furin substrate as an off-white solid. TLC (10% methanol/dichloromethane) Rf=0.00.

EXAMPLE 15

Preparation of a Fluorescein-Based Esterase Substrate Targeted to the Endoplasmic Reticulum, Producing Green Fluorescence Upon Enzyme Activity 5(6)-carboxy-2',7'-dichlorofluorescein (M1239)

To a 500 mL round-bottom flask was added trimellitic anhydride (9.61 g, 50.0 mmol), 4-chlororesorcinol (14.56 g, 100 mmol) and methanesulfonic acid (30 mL). The resulting solution was heated to 120° C. After 16 h, the solution was poured into ice-cold water (800 mL). The resulting orange precipitate was collected via vacuum filtration, rinsing the precipitate with water until a filtrate with a neutral pH was achieved. The product was dried in vacuo to give M1239 (21.7 g, 48.7 mmol, 97%) as an orange solid. TLC (9:1:1 dichloromethane/methanol/acetic acid) Rf=0.68.

5(6)-carboxy-2',7'-dichlorofluorescein, NHS Ester (M1243)

To a 50 mL round-bottom flask was added M1239 (2.23 g, 5.0 mmol) and N,N-dimethylformamide (5.0 mL), followed by pyridine (0.607 mL, 7.50 mmol). After 5 min, M1027 (1.58 g, 7.50 mmol) was added. After 17 h, TLC monitoring showed insufficient product formation. Additional M1027 (1.58 g, 7.50 mmol) and pyridine (0.606 mL, 7.50 mmol) were added. After 2 h, TLC monitoring continued to show insufficient product formation. Additional M1027 (0.79 g, 3.75 mmol) and pyridine (0.303 mL, 3.75 mmol) were added. After 2 h, the reaction solution was diluted with ethyl acetate (500 mL) and washed with water (500 mL), 1.0 N aq. HCl (2×200 mL) and saturated. aq. $NaHCO_3$ (500 mL). The organic layer was dried with $MgSO_4$ and concentrated to a small volume in vacuo. The product was then precipitated from diethyl ether (500 ml) and petroleum ether (200 mL). The resulting precipitate was collected via vacuum filtration and dried in vacuo to give M1243 (2.04 g, 3.76 mmol, 75%) as an orange solid. TLC (9:1:1 dichloromethane/methanol/acetic acid) Rf=0.79.

5(6)-(4-maleimidobutanecarboxamido)-2',7'-dichlorofluorescein (M1972)

To a flame-dried 100 mL round-bottom flask was added 5(6)-carboxy-2',7'-dichlorofluorescein NHS ester (543.0 mg, 1.00 mmol) and N,N-dimethylformamide (5.0 mL). In a 20 mL vial, a separate solution was prepared with 4-maleimido-1-butanamine hydrochloride (422.8 mg, 1.50 mmol) and diisopropylethylamine (5 drops) in N,N-dimethylformamide (4.0 mL). The 4-maleimido-1-butanamine hydrochloride solution was added to the carboxyfluorescein solution. After 19 h, additional diisopropylethylamine (0.340 mL, 2.00 mmol) was added. After 6.5 h, the solution was diluted with ethyl acetate (200 mL) and washed with 1.0 N aq. HCl (3×100 mL), then saturated. aq. $NaHCO_3$ (3×100 mL); the desired product partitioned into the aqueous layer. The aqueous layer was washed with ethyl acetate (3×50 mL), then re-acidified with 1.0 N aq. HCl until pH<1 obtained. The product was extracted from the acidic aqueous environment with ethyl acetate (3×100 mL), and the organic layer was washed with saturated. aq. NaCl (200 mL), dried over MgSO$_4$ and concentrated in vacuo. The product was purified via flash chromatography over SiO$_2$, eluting with 0% to 100% acetone/dichloromethane, followed by 0% to 20% methanol/acetone. The purified product was concentrated in vacuo, dissolved in a minimum of methanol and precipitated from hexanes. The precipitate was collected via vacuum filtration and dried in vacuo to give M1972 (112.4 mg, 0.190 mmol, 19%) as a red/orange solid. TLC (10% methanol/ethyl acetate) Rf=0.48; $^1$H NMR (DMSO-d$_6$, 300 MHz): δ=11.14 (s, 2H), 8.84 (br s, 0.5H), 8.69 (br s, 0.5H), 8.46 (s, 0.5H), 8.26 (d, J=8.2 Hz, 0.5H), 8.17 (d, J=8.0 Hz, 0.5H), 8.10 (d, J=7.9 Hz, 0.5H), 7.68 (s, 0.5H), 7.44 (d, J=8.2 Hz, 0.5H), 7.04 (s, 1H), 6.99 (s, 1H), 6.93 (s, 2H), 6.76 (s, 2H), 3.47 (t, J=6.2H, 2H), 3.32 (m, 1H), 3.20 (m, 1H), 1.51 (m, 4H).

5(6)-(4-maleimidobutanecarboxamido)-2',7'-dichlorofluorescein bis-acetate (M2388)

To a 4 mL vial containing M1972 (60.3 mg, 102 μmol) was added dichloromethane (2.0 mL), followed by acetic anhydride (0.50 mL) and pyridine (0.50 mL). After 2 h, the solution was diluted in dichloromethane (10 mL) and washed with 1.0 N HCl (2×5 mL), saturated. aq. NaHCO$_3$ (2×5 mL) and saturated. aq. NaCl (10 mL). The organic layer was dried over MgSO$_4$ and concentrated in vacuo, co-evaporating with toluene (15 mL). The resulting yellow oil was dissolved in dichloromethane (1 mL), diluted with diethyl ether (20 mL) and precipitated with hexanes (50 mL). The resulting precipitate was collected via vacuum filtration and dried in vacuo to give M2388 (15.4 mg, 22.7 μmol, 22%) as a pale yellow solid. TLC (10% methanol/dichloromethane) Rf=0.71; $^1$H NMR (CDCl$_3$, 300 MHz): δ=8.40 (s, 0.5H), 8.23 (dd, J=8.0, 1.5 Hz, 0.5H), 8.13 (d, J=0.9 Hz, 1H), 7.55 (s, 0.5H), 7.30 (d, J=8.2 Hz, 0.5H), 7.16 (d, J=7.1 Hz, 2H), 6.84 (d, J=2.4 Hz, 2H), 6.72 (s, 1H), 6.65 (s, 1H), 6.54 (t, J=5.0 Hz, 1H), 3.62-3.46 (m, 4H), 2.37 (s, 6H), 1.74-1.60 (m, 4H).

5(6)-(4-maleimidobutanecarboxamido)-2',7'-dichlorofluorescein bis-acetate Conjugated to ER-Targeting Peptide (M2391)

To a 1.5 mL Eppendorf tube was added a solution of M2388 (100 μL, 2.0 mM in acetone, 0.2 μmol), a solution of AcHN—C—F—F—K-D-E-L-COOH (SEQ ID NO:6) (100 μL, 1.0 mmol in 1:1 ethanol/water, 0.1 μmol) and a solution of triethylamine (100 μL, 0.10 mM in water, 0.010 μmol). Upon observing M2388 precipitate from solution, ethanol (50.0 μL) was added to the Eppendorf to aid dissolution. After gently agitating for 18 h, the solution was diluted with water and extracted with dichloromethane (3×500 μL) and ethyl acetate (1×500 μL). The aqueous layer was lyophilized to give M2391 (mass and yield not determined). TLC (10% methanol/dichloromethane) Rf=0.00.

EXAMPLE 16

Preparation of a Fluorescein-Based Esterase Substrate Targeted to the Golgi Apparatus, Producing Green Fluorescence Upon Enzyme Activity 5(6)-(4-maleimidobutanecarboxamido)-2',7'-dichlorofluorescein bis-acetate Conjugated to Golgi-Targeting Peptide (M2392)

To a 1.5 mL Eppendorf tube was added a solution of M2388 (100 μL, 2.0 mM in acetone, 0.2 μmol), a solution of H$_2$N-G-A-S-D-Y-Q-R-L-C—COOH (SEQ ID NO:7) (100 μL, 1.0 mmol in water, 0.1 μmol) and a solution of triethylamine (100 μL, 0.10 mM in water, 0.010 μmol). Upon observing M2388 precipitate from solution, ethanol (50.0 μL) was added to the Eppendorf to aid dissolution. After gently agitating for 18 h, the solution was diluted with water and extracted with dichloromethane (3×500 μL) and ethyl acetate (1×500 μL). The aqueous layer was lyophilized to give M2392 (mass and yield not determined). TLC (10% methanol/dichloromethane) Rf=0.00.

EXAMPLE 17

Preparation of Cells in Culture for Labeling.

Human skin fibroblasts from a healthy specimen and from Gaucher diseases patients were obtained from the Coriell Institute for Medical Research (Camden, N.J.). Cells were maintained in Minimum Essential Medium Eagle (EMEM) (Hyclone) supplemented with 10% Fetal Bovine Serum (Atlanta Biologicals) and 1× Antibiotic/Antimycotic (Tokue). Cells were grown to 90% confluence and passaged by splitting at a 1:5 ratio. Cells were incubated at 37° C., with 5% CO$_2$ atmosphere.

EXAMPLE 18

Preparation of Labeling Solutions for Mammalian Cell Systems.

The substrates of the invention are separately dissolved in DMSO to prepare a 10 mM stock solutions. These stock solutions were kept sealed in small aliquots, and stored at −20° C. prior to use. Each stock solution was kept frozen at all times until use, and exposure to light minimized. One aliquot of dye stock was taken from the freezer immediately before an experiment and thawed completely at room temperature. The labeling solution was then prepared by adding the dye stock solution to fresh serum-free culture medium (37° C.) in an amount sufficient to make final dye concentrations ranging from 1-200 μM. Dye stock solutions were added such that the final concentration of DMSO in the labeling solution does not exceed 2%. Cell samples to be stained were grown to exponential growth phase in an incubator at 37° C. in 5% CO$_2$, the media removed by suction and the cells washed with PBS (2×) prior to addition of the staining solutions (in culture media as above) containing the appropriate substrates and incubation as above for time periods of between 5 minutes and 24 hours prior to analysis by fluorescence microscopy.

EXAMPLE 19 Labeling of Endoplasmic Reticulum with Targeted Resorufin Based Mannosidase Substrate Healthy human lung fibroblasts (AG06173, Coriell Institute for Medical Research, Camden, N.J.) were prepared according to Example 17 were grown to 70% confluency in optical bottom 96 well plates, the culture media was then replaced with media containing 6.25 uM M2496 (Endoplasmic Reticulum) and 25 uM M2497 (Golgi Apparatus targeted) alpha-mannosidase substrates in serum free EMEM for 16 hours at 37° C., 5% CO$_2$.

Upon completion of incubation time cells were washed in PBS and bathed in Opti-Klear™ Imaging Buffer (Marker Gene Technologies, Inc Eugene Oreg.) with or without nuclear stain Hoechst 33342. Cells were then imaged on an EVOS Auto-FL fluorescence microscope (Life Technologies) fitted with a TexasRed™ light cube.

Bright red organelle specific staining was observed with minimal background staining of the cytosol (FIG. 1).

EXAMPLE 20

Labeling of Endoplasmic Reticulum with Targeted Resorufin Based Glucosidase Substrate.

Gaucher Type II human fibroblast cells (cell line GM02627, Coriell Institute for Medical Research, Camden, N.J., a lysosomal storage disease where mutant β-Glucocerebrosidase enzyme causes an accumulation of the enzyme in the ER) and healthy (AG06173) human fibroblasts were prepared according to Example 17 and grown to 70% confluency in optical bottom 96 well plates. Each cell line was stained with 12.5 uM of substrate M2550 in serum free media overnight at 37 C, 5% CO2.

Following incubation cells were washed in PBS and bathed in Opti-Klear™ Imaging Buffer (Marker Gene Technologies, Inc Eugene Oreg.). Cells were then imaged on EVOS Auto-FL fluorescence microscope (Life Technologies) fitted with a TexasRed™ light cube.

Staining patterns exhibited the increased levels of mutant beta-Glucocerebrosidase enzyme trapped in the ER of Gaucher Type II cells (FIG. 3).

EXAMPLE 21

Staining of the Endoplasmic Reticulum with Targeted Resorufin Based Glucosidase Substrate and Staining Nucleus in Living Cells Using an Additional Detection Reagent.

Cells were stained according to Example 18. After the PBS wash the nucleic acid stain Hoeschst 33342 was added to the imaging buffer at 1 ug/mL and the cells were incubated at 37° C. in 5% $CO_2$ for 5 minutes. Cells were then imaged using appropriate filter sets such as Texas Red for ER staining and DAPI for nuclear staining.

Bright red organelle specific staining and blue nuclear staining was observed with minimal background staining of the cytosol.

EXAMPLE 22

Staining of the Endoplasmic Reticulum with Targeted Resorufin Based Glucosidase Substrate, Co-Staining with Endoplasmic Reticulum Specific Dye and Staining Nucleus in Living Cells Using an Additional Detection Reagent.

Gaucher Type II (GM02627 human fibroblasts) prepared as described herein were stained with either 10 uM M2550 or 50 uM M2496 in serum free media and incubated overnight at 37° C., 5% $CO_2$. Following incubation the staining media was removed and serum free media containing 5 ug/ml DiOC6(3) was added and incubated for 5 minutes at 37° C.

Cells were washed in PBS and bathed in Opti-Klear™ Imaging Buffer (Marker Gene Technologies, Inc Eugene Oreg.). Cells were then imaged on EVOS Auto-FL fluorescence microscope (Life Technologies) fitted with GFP and TexasRed™ light cubes. Staining patterns exhibited colocalization of the ER targeted substrates with the known ER stain DiOC6(3) (FIG. 4).

EXAMPLE 23

Triple Labeling of Endoplasmic Reticulum, Lysosomes and Nuclei in Living Cells

Normal cells and those from a Gaucher disease patient prepared according to Example 17 were grown to 70% confluency in optical bottom 96 well plates, the culture media was then replaced with media containing a lysosome specific glucosidase substrate and incubated at 37° C. and 5% $CO_2$ for 16 hours. The staining media was then replaced with the endoplasmic reticulum substrate at 20 uM as Example 18 and incubated at 37° C. for 4 hours. The cells were then washed 3 times with PBS. The nucleic acid stain Hoeschst 33342 was added to the imaging buffer at 1 ug/mL and the cells were incubated at 37° C. for 5 minutes. Cells were then imaged using appropriate filter sets such as Texas Red for ER staining, GFP for lysosomal staining and DAPI for nuclear staining.

Normal cells showed an increased amount of green punctuate staining and less red organelle staining where diseased cells showed reduced lysosomal staining and greater red staining in the endoplasmic reticulum. Both cell types showed bright blue nuclear staining.

EXAMPLE 24

Staining of Endoplasmic Reticulum with Targeted Resorufin Based Mannosidase Substrate after Incubation with Mannosidase Inhibitor.

Normal, healthy human lung fibroblasts (Cell line AG06173, Coriell Institute for Medical Research, Camden, N.J.) were prepared according to example 17 and plated in an optical bottom 96 well plate at $1 \times 10^4$ cells/mL.

Cells were then incubated at 37° C. and 5% $CO_2$ in complete EMEM and incubated for 1 (Golgi) or 5 days (ER) at 37° C., 5% $CO_2$ with or without the mannosidase inhibitor swainsonine at 100 uM. The appropriate targeted substrate for staining either the ER or Golgi was then applied at a final concentration of 20 uM and incubated for 4 hours at 37° C., 5% $CO_2$.

Following incubation the cells were washed in PBS and bathed in Opti-Klear™ Imaging Buffer (Marker Gene Technologies, Inc Eugene Oreg.) with or without nuclear stain Hoechst 33342. Cells were then imaged on an EVOS Auto-FL fluorescence microscope (Life Technologies) fitted with a TexasRed™ light cube.

Staining patterns exhibited a reduction in enzyme activity upon swainsonine inhibitor application (FIG. 2).

It is to be understood that, while the foregoing invention has been described in detail by way of illustration and example, numerous modifications, substitutions, and alterations are possible without departing from the spirit and scope of the invention as described in the following claims.

What is claimed is:

1. A substrate for detecting enzyme activity in a sample containing cellular organelles, wherein said substrate comprises a formula selected from the group consisting of:

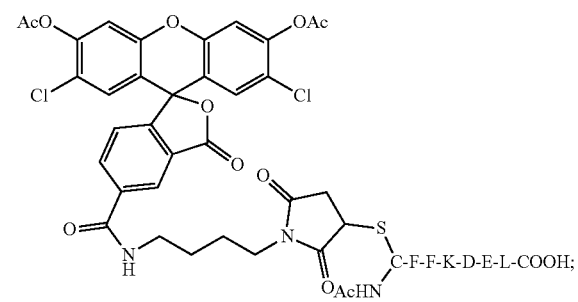

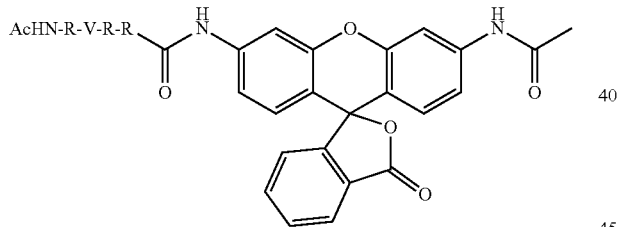

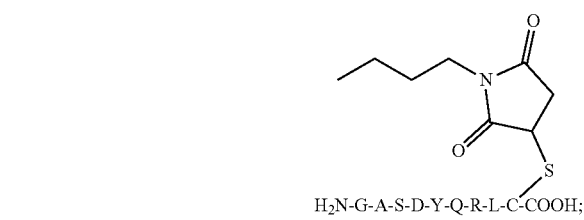

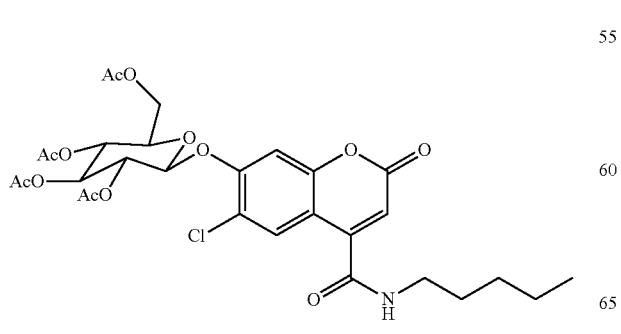

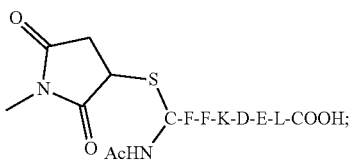

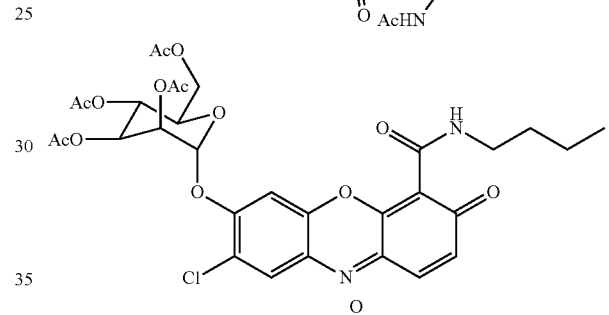

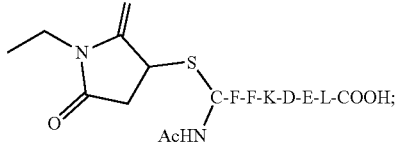

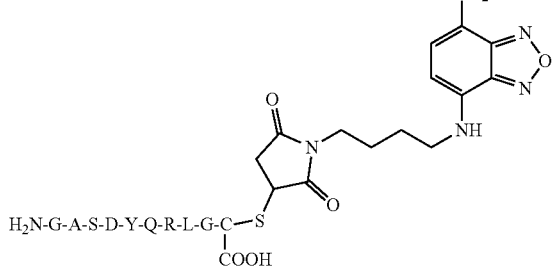

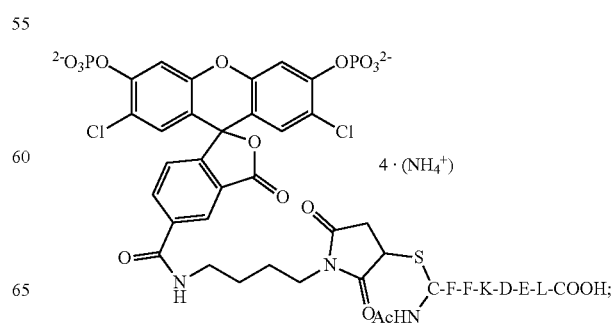

-continued

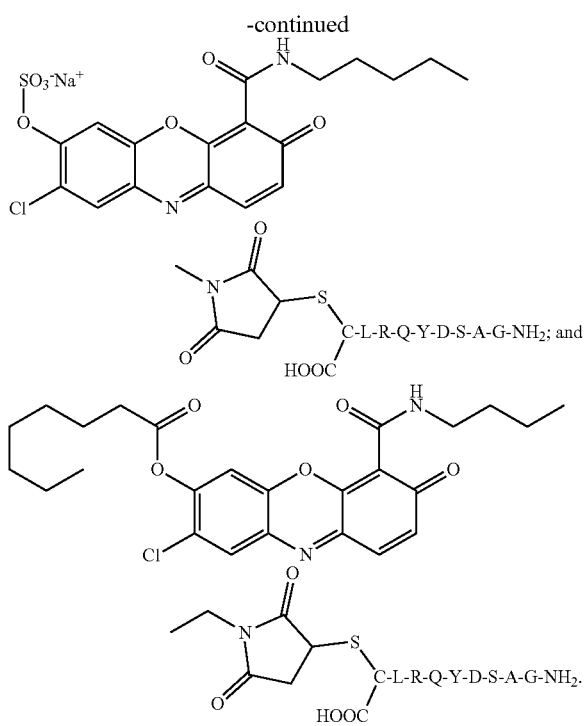

2. A substrate for detecting enzyme activity in a sample containing cellular organelles having the formula:

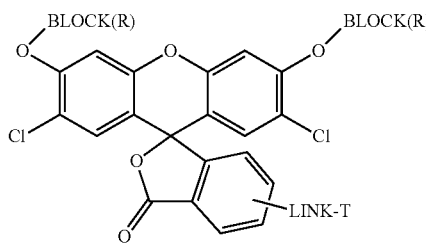

A) T is a peptide having an amino acid sequence selected from the group consisting of: SEQ ID NO:2, SEQ ID NO:4, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:25, and SEQ ID NO:26;

B) BLOCK is a monovalent moiety adapted to be cleaved from the remainder of the substrate by action of a specific enzyme native to said organelle, resulting in a visible signal at the site of the enzyme reaction;

C) LINK is a covalent linkage; and

D) (R) is a substituent selected from the group consisting of hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl, an unsubstituted carboxylic acid ester and an alkoxy substituted carboxylic acid ester.

3. The substrate of claim 2, wherein said organelle is selected from the group consisting of lysosomes, nucleus, peroxisomes, the Golgi apparatus and the Endoplasmic Reticulum.

4. The substrate of claim 2, wherein substituent (R) is selected from the group consisting of an unsubstituted carboxylic acid ester and an alkyloxy substituted carboxylic acid ester.

5. The substrate of claim 2, where BLOCK is selected from the group consisting of: (i) a monovalent moiety derived by removal of a hydroxy group from phosphate or sulfate, (ii) a biologically compatible salt of (i); (iii) a monovalent moiety derived by removal of a hydroxy group from a carboxy group of an aliphatic, aromatic or amino acid or of a peptide; and (iv) a monovalent moiety derived by removal of an anomeric hydroxy group from a mono- or polysaccharide.

6. The substrate of claim 2, where LINK comprises from 1 to 20 non-hydrogen atoms selected from the group consisting of C, N, O and S.

7. The substrate of claim 2, where LINK comprises from 1 to 6 carbon atoms.

8. The substrate of claim 2, where LINK has the formula $-(CH_2)_a(CONH(CH_2)_b)_z-$, where a is an integer 0-5, b is 1-5 and z is 1.

9. A substrate for detecting enzyme activity in a sample containing cellular organelles having a formula selected from the group consisting of:

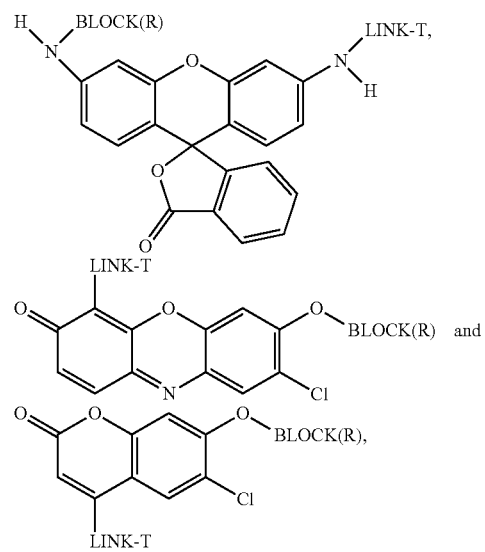

where

A) T is a peptide having an amino acid sequence selected from the group consisting of: SEQ ID NO: 1, SEQ ID NO:2, SEQ ID NO:4, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:25, and SEQ ID NO:26;

B) BLOCK is a monovalent moiety adapted to be cleaved from the remainder of the substrate by action of a specific enzyme native to said organelle, resulting in a visible signal at the site of the enzyme reaction;

C) LINK is a covalent linkage; and

D) (R) is a substituent selected from the group consisting of hydrogen, halogen, cyano, alkyl, substituted methane, perhalogenated alkyl, perfluoroalkyl, halomethyl, alkoxy, cycloalkyl, arylalkyl, acyl, aryl, heteroaryl, alkenyl, an unsubstituted carboxylic acid ester and an alkoxy substituted carboxylic acid ester.

10. The substrate of claim 9, wherein said organelle is selected from the group consisting of lysosomes, nucleus, peroxisomes, the Golgi Apparatus and the Endoplasmic Reticulum.

11. The substrate of claim 9, wherein substituent (R) is selected from the group consisting of an unsubstituted carboxylic acid ester and an alkyloxy substituted carboxylic acid ester.

12. The substrate of claim 9, where BLOCK is selected from the group consisting of: (i) a monovalent moiety derived by removal of a hydroxy group from phosphate or sulfate, (ii) a biologically compatible salt of (i); (iii) a monovalent moiety derived by removal of a hydroxy group from a carboxy group of an aliphatic, aromatic or amino acid or of a peptide; and (iv) a monovalent moiety derived by removal of an anomeric hydroxy group from a mono- or polysaccharide.

13. The substrate of claim 9, where LINK comprises from 1 to 20 non-hydrogen atoms selected from the group consisting of C, N, O and S.

14. The substrate of claim 9, where LINK comprises from 1 to 6 carbon atoms.

15. The substrate of claim 9, where LINK has the formula —$(CH_2)_a(CONH(CH_2)_b)_z$—, where a is an integer 0-5, b is 1-5 and z is 1.

* * * * *

SEQUENCE LISTING

<160> NUMBER OF SEQ ID NOS: 26

<210> SEQ ID NO 1
<211> LENGTH: 4
<212> TYPE: PRT

```
<213> ORGANISM: Artificial Sequence
<220> FEATURE:
<223> OTHER INFORMATION: Target Sequence 1

<400> SEQUENCE: 1

Lys Asp Glu Leu
1

<210> SEQ ID NO 2
<211> LENGTH: 6
<212> TYPE: PRT
<213> ORGANISM: Artificial Sequence
<220> FEATURE:
<223> OTHER INFORMATION: Target Sequence 2

<400> SEQUENCE: 2

Ser Asp Tyr Gln Arg Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Target Sequence3

<400> SEQUENCE: 3

Pro Lys Lys Lys Arg Lys Val
1               5

<210> SEQ ID NO 4
<211> LENGTH: 7
<212> TYPE: PRT
<213> ORGANISM: Artificial Sequence
<220> FEATURE:
<223> OTHER INFORMATION: Target Sequence

<400> SEQUENCE: 4

Cys Lys Gly Gly Ala Lys Leu
1               5

<210> SEQ ID NO 5
<211> LENGTH: 11
<212> TYPE: PRT
<213> ORGANISM: Artificial Sequence
<220> FEATURE:
<223> OTHER INFORMATION: Target Sequence 5

<400> SEQUENCE: 5

Val Val Val Lys Lys Lys Arg Lys Val Val Cys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Target Sequence 6

<400> SEQUENCE: 6

Cys Phe Phe Lys Asp Glu Leu
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Target Sequence 7

<400> SEQUENCE: 7

Gly Ala Ser Asp Tyr Gln Arg Leu Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Target Sequence 8

<400> SEQUENCE: 8

Cys Ala His His Ala Glu Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Target Sequence 9

<400> SEQUENCE: 9

Cys Ala Arg His Ala Glu Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Target Sequence 10

<400> SEQUENCE: 10

Cys Pro Leu His Asn Glu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Target Sequence 11

<400> SEQUENCE: 11

Cys Glu Arg His Thr Glu Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Target Sequence 12

<400> SEQUENCE: 12

Cys Thr Glu His Ile Glu Leu
1               5

<210> SEQ ID NO 13
<211> LENGTH: 7
<212> TYPE: PRT
<213> ORGANISM: Artificial Sequence
<220> FEATURE:
```

```
<223> OTHER INFORMATION: Target Sequence 13

<400> SEQUENCE: 13

Cys Thr Glu His Val Glu Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Target Sequence 14

<400> SEQUENCE: 14

Ser Asp Tyr Gln Arg Leu Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Target Sequence 15

<400> SEQUENCE: 15

Ala Asp Tyr Gln Arg Leu Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Target Sequence 16

<400> SEQUENCE: 16

Ser Gly Tyr Gln Arg Leu Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Target Sequence 17

<400> SEQUENCE: 17

Ala Ala Tyr Gln Arg Leu Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Target Sequence18

<400> SEQUENCE: 18

Ser Asp Tyr Glu Arg Leu Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Target Sequence 19
```

```
<400> SEQUENCE: 19

Ser Asp Tyr Gln Arg Val Cys
1               5

<210> SEQ ID NO 20
<211> LENGTH: 11
<212> TYPE: PRT
<213> ORGANISM: Artificial Sequence
<220> FEATURE:
<223> OTHER INFORMATION: Target Sequence 20

<400> SEQUENCE: 20

Val Val Val Lys Lys Arg Arg Arg Val Val Cys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Target Sequence 21

<400> SEQUENCE: 21

Val Val Val Lys Lys Arg Lys Lys Val Val Cys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Target Sequence

<400> SEQUENCE: 22

Cys Lys Gly Gly Tyr Gln Ser Lys Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Target Sequence 23

<400> SEQUENCE: 23

Cys Lys Gly Gly Tyr Gln Ser Glu Leu
1               5

<210> SEQ ID NO 24
<211> LENGTH: 7
<212> TYPE: PRT
<213> ORGANISM: Artificial Sequence
<220> FEATURE:
<223> OTHER INFORMATION: Target Sequence 24

<400> SEQUENCE: 24

Cys Gly Gly Gly Gly Gly Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Target Sequence 25
```

```
<400> SEQUENCE: 25

Lys Lys Lys Arg Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Target Sequence 26

<400> SEQUENCE: 26

Ser Cys Tyr Gln Arg Leu
1               5
```